United States Patent
Stemmer

(10) Patent No.: US 9,138,162 B2
(45) Date of Patent: Sep. 22, 2015

(54) MAGNETIC RESONANCE METHOD AND APPARATUS FOR OBTAINING A SET OF MEASURED DATA RELATING TO A BREATHING OBJECT OF INTEREST

(71) Applicant: Alto Stemmer, Erlangen (DE)

(72) Inventor: Alto Stemmer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 235 days.

(21) Appl. No.: 13/866,311

(22) Filed: Apr. 19, 2013

(65) Prior Publication Data

US 2013/0281824 A1    Oct. 24, 2013

(30) Foreign Application Priority Data

Apr. 20, 2012 (DE) .......................... 10 2012 206 578

(51) Int. Cl.
- *A61B 5/055* (2006.01)
- *A61B 5/08* (2006.01)
- *G01R 33/565* (2006.01)
- *A61B 5/00* (2006.01)
- *A61B 5/113* (2006.01)
- *G01R 33/567* (2006.01)

(52) U.S. Cl.
CPC . *A61B 5/055* (2013.01); *A61B 5/08* (2013.01); *A61B 5/7289* (2013.01); *G01R 33/56509* (2013.01); *A61B 5/1135* (2013.01); *G01R 33/5676* (2013.01)

(58) Field of Classification Search
CPC ........ A61B 5/055; A61B 5/08; A61B 5/1135; A61B 5/7289; G01R 33/56509; G01R 33/5676
See application file for complete search history.

(56) References Cited

U.S. PATENT DOCUMENTS

| 7,039,451 B1 | 5/2006 | Jhooti et al. |
| 2011/0130644 A1 | 6/2011 | Stemmer |
| 2011/0152668 A1* | 6/2011 | Stemmer ...................... 600/413 |
| 2012/0271155 A1* | 10/2012 | Stemmer ...................... 600/413 |

OTHER PUBLICATIONS

Jhooti et al., "Phase Ordering With Automatic Window Selection (PAWS): a Novel Motion-Resistant Technique for 3D Coronary Imaging," Magnetic Resonance in Medicine, vol. 43, pp. 470-480, (2000).

Kolbitsch, "Highly Efficient Whole-Heart Imaging Using Radial Phase Encoding-Phase Ordering With Automatic Window Selection," Magnetic Resonance in Medicine, vol. 66, pp. 1008-1018, (2011).

Lewis et al., "Comparison of Respiratory Triggering and Gating Techniques for the Removal of Respiratory Artifacts in MR Imaging," Radiology vol. 160, pp. 803-810, (1986).

Nguyen et al., "Free-breathing 3D steady-state free precession coronary magnetic resonance angiography: Comparison of four navigator gating techniques," Magnetic Resonance Imaging, vol. 27, No. 6, pp. 807-814, (2009).

(Continued)

*Primary Examiner* — Ruth S Smith
(74) *Attorney, Agent, or Firm* — Schiff Hardin LLP

(57) ABSTRACT

In a method for acquisition of a measurement data set of a respirating examination subject by magnetic resonance technology, the measurement data set is acquired by numerous individual measurements, wherein, for each individual measurement, a respiratory position and a respiratory phase are determined, based on which it is decided whether the individual measurement is to be included in the final measurement data set from which an image data set is reconstructed.

13 Claims, 10 Drawing Sheets

(56) References Cited

OTHER PUBLICATIONS

Nuval et al., "Refined PAWS Algorithms for 3D Coronary MRA," Intl. Soc. Mag. Reson. Med., vol. 11, p. 1625, (2003).

Sachs et al., "The Diminishing Variance Algorithm for Real-Time Reduction of Motion Artifacts in MRI," Magnetic Resonance in Medicine, vol. 34, pp. 412-422, (1995).

Sachs et al., "Real-Time Motion Detection in Spiral MRI Using Navigators," Magnetic Resonance in Medicine, vol. 32, pp. 639-645, (1994).

Stemmer, "Phase Navigator for respiratory triggering," Healthcare Sector, Siemens AG, Erlangen, Germany, (1994).

Stemmer et al., "Respiratory Gated VIBE Sequence," Healthcare Sector, Siemens AG, Erlangen, Germany, Republic of Korea.

Wang et al., "Navigator-Echo-based Real-Time Respiratory Gating and Triggering for Reduction of Respiration Effects in Three-dimensional Coronary MR Angiography," Cardiac Radiology, Radiology vol. 198, pp. 55-61, (1996).

* cited by examiner

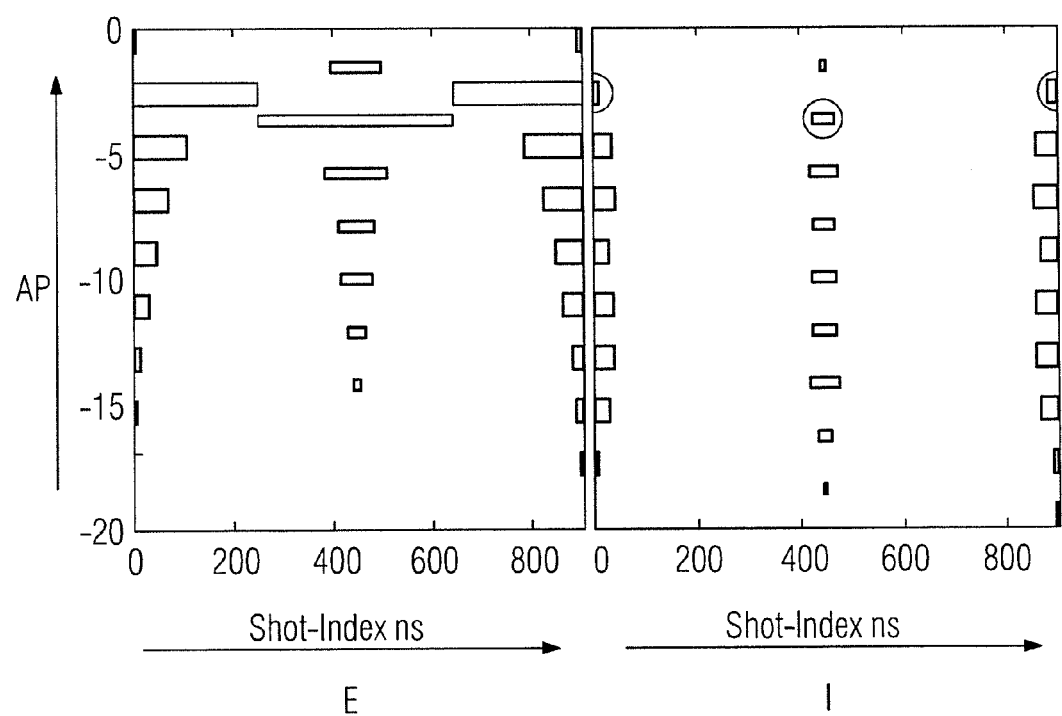

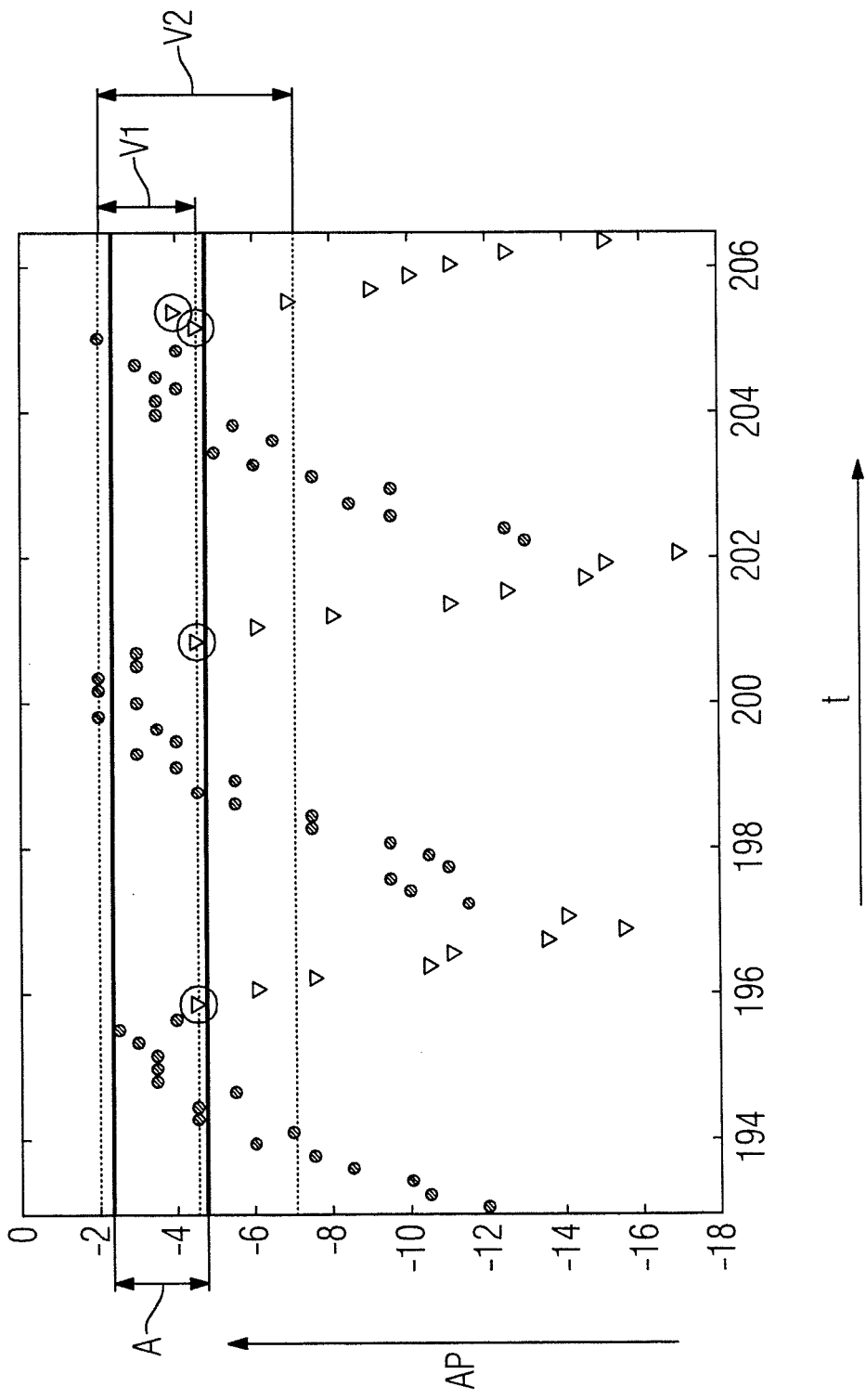

MAGNETIC RESONANCE METHOD AND APPARATUS FOR OBTAINING A SET OF MEASURED DATA RELATING TO A BREATHING OBJECT OF INTEREST

BACKGROUND OF THE INVENTION

1. Field of the Invention

The invention relates to a method for the acquisition of a measurement data set for a respirating examination subject by means of magnetic resonance technology, and a magnetic resonance apparatus, and a computer-readable data storage medium for implementing such a method.

2. Description of the Prior Art

Magnetic resonance (MR) is a known technology with which images from the interior of an examination subject can be generated. Expressed simply, the examination subject is placed in a magnetic resonance imaging scanner, in a strong, static, homogenous base magnetic field, also called a $B_0$ field, having a field strength of 0.2 tesla-7 tesla and more, such that the nuclear spins of the subject orient themselves along the base magnetic field. In order to trigger magnetic resonance signals, the examination subject is irradiated with high frequency excitation pulses (RF pulses), the triggered magnetic resonance signals are detected and entered into a memory that represents a mathematical domain known as k-space, and MR images are reconstructed on the basis of the k-space data, or spectroscopy data are determined. For the spatial encoding of the measurement data, rapidly activated magnetic gradient fields are superimposed on the base magnetic field. The recorded measurement data are digitized and stored as complex number values in a k-space matrix. From the k-space matrix populated with data values in this manner, an associated MR image can be reconstructed, for example, by means of a multi-dimensional Fourier transformation.

The respiratory movement of a patient that is to be examined by means of MR can lead to so-called ghosting, to blurring, and/or to intensity losses in the images generated, as well as registration errors between generated images particularly in an examination of the organs of the thorax and the abdomen, i.e. of examination regions affected by respiratory movement. These artifacts can make it difficult for a physician to perform an analysis on the basis of the images, and can lead to lesions being overlooked, for example. Numerous techniques exist in the prior art for reducing artifacts resulting from respiratory movement. One of these techniques is respiratory gating. Respiratory gating is a technique with which, during the MR measurement, the respiration of the patient is recorded and assigned to the acquired measurement data. With respiratory gating, only measurement data are then used for reconstruction for which the associated recorded respiratory movement fulfills certain specifiable criteria.

The respiration of the patient can be detected with external sensors, e.g. a pneumatic cuff or belt, or with MR signals, so-called navigators. A navigator is normally a short sequence of the MR signals, e.g. acquired from the diaphragm or other signal sources in the examination subject, the movement of which is correlated to the respiration of the patient. The respiratory movement can be reproduced from the position of the diaphragm or the other signal sources. The respiratory position is normally (but not necessarily) determined solely from the data recorded with two navigator sequences. The one navigator sequence is a reference measurement (normally the first navigator sequence), for the other navigator measurement, which is assigned to the determined respiration position.

In the following, reference shall be made to respiration triggers, with or without navigators. Respiration triggering is understood in this context as a technique that synchronizes the image generating MR measurement with the respiration of the freely respirating patients, and with which it is attempted to acquire a defined packet of measurement data during a distinctive phase of the respiratory cycle. If, in doing so, a specific layer is excited only once for each triggering, then the effective TR (the time period between successive excitations of a layer) of the sequence is the same, or is a multiple of the average respiratory cycle of the patient. In contrast, with respiratory gating, the repetition rate, particularly the TR thereof, is independent of the respiration of the patient. The repetition rate is controlled, rather, by means of a parameter, or by means of an additional physiological signal, e.g. an ECG.

For respiratory triggers with navigators, monitoring phases, during which the navigator sequence for recording the respiratory signal is repeated, alternate with measurement phases, during which the imaging sequence is carried out. During the monitoring phases, the imaging sequence is normally not carried out. In this respect, the temporal scanning rate of the respiratory movement is only limited in terms of a lower limit by the duration of the navigator sequence. The scanning rate is therefore normally higher than with respiratory gating.

If the respiratory signal is recorded using an external sensor, e.g. a pneumatic belt, then the scanning rate of the physiological signal is normally substantially higher than with the use of navigator measurements, such that digital filters and temporal averaging is normally possible. Furthermore, for a measurement of the physiological signal, the imaging measurement must be uninterrupted. Accordingly, with respiratory gating using an external signal, the acceptance window is not defined as a function of the respiratory position, but instead, is normally defined as a time window. The opening of the time window occurs, for example, when the measured physiological signal (which is a function of the chest measurement when a respiratory belt is used), falls below a threshold during the exhalation, and closes when this threshold is again exceeded during an inhalation (see, e.g. Craig E. Lewis et al. "Comparison of Respiratory Triggering and Gating Techniques for the Removal of Respiratory Artifacts in MR Imaging;" Radiology 1986; 160, Pages 803-810).

In the following, primarily respiratory gating methods, with a recording of the respiratory position by means of navigator measurement, shall be considered. For respiratory gating with navigators, the navigator sequence is interlaced with the imaging sequence, for example, and a diaphragm position measured using a navigator is subsequently assigned to the imaging data acquired directly thereafter (or before).

A distinction is made between retrospective and prospective respiratory gating.

With retrospective respiratory gating the respiratory movement is detected and recorded during the MR measurement, but not evaluated. Instead, the k-space that is to be recorded is measured repeatedly. For the reconstruction, only a portion of the measured data are referenced, preferably that data in which the respiratory signal lies within a specific window for a distinctive respiratory position. If a specific k-space data point that is necessary for the image reconstruction is repeatedly measured within the distinctive window, then the data can be averaged. If, instead, a data point is always measured outside of the window, then that data point deviating the least from the distinctive position can be used for the reconstruction.

With prospective respiratory gating, the physiological respiratory signal measured using a respiratory sensor (e.g. the diaphragm position measured with a navigator sequence) is evaluated during the measurement, and the MR measurement is controlled, based on the recorded physiological signal. In the simplest embodiment, the so-called acceptance/rejection algorithm (ARA), the measurement of an imaging data packet (and if applicable, the associated navigator sequence) is repeated until the physiological signal falls within a previously defined acceptance window.

One example of an acceptance/rejection algorithm of this type and, at the same time, the first description of respiratory gating with navigators, is described in the article by Todd S. Sachs, Craig H. Meyer, Bob S. Hu, Jim Kohli, Dwight G. Nishimura and Albert Macovski: "Real-Time Motion Detection in Spiral MRI Using Navigators," MRM 32: Pages 639-645 (1994). The authors acquired one or more navigators for each excitation of a spiral sequence. The navigators were acquired here following the acquisition of the image data. Different navigators are distinguished by their spatial orientation. From each navigator, a spatial displacement along the axis of the navigator in relation to a reference navigator is calculated using a cross-correlation. The navigator scan acquired following the first imaging scan is used, in each case, as a reference. A specific imaging scan is repeated until the spatial displacement determined with the navigator, in relation to the reference, is less than a threshold value provided by a user. This, therefore, relates to an acceptance/rejection algorithm based on one or more spatial displacements.

Another example of an acceptance/rejection algorithm is described by Wang et al. in "Navigator-Echo-Based Real-Time Respiratory Gating and Triggering for Reduction of Respiratory Effects in Three-Dimensional Coronary MR Angiography," Radiology 198; Pages 55-60 (1996). In this case, the physiological signal is the displacement of the diaphragm position, determined with a navigator, in relation to a reference state. One difference from the work by Sachs et al. is that, in each case, a navigator is acquired before and after the imaging scan, and that the imaging scan is then only accepted if the displacement determined by means of both navigators is less than the threshold value.

In order to determine the acceptance window, a so-called pre-scan is normally carried out for each patient, in which the respiratory movement is recorded, for example, with the navigator sequence, but imaging data are not yet acquired.

Prospective respiratory gating is normally more efficient than retrospective respiratory gating. A prerequisite for prospective respiratory gating is a real-time capability of the normally-provided control software for the MR apparatus. For this purpose, real-time capability means that data measured with the sequence (in this case, the sequence comprises imaging and navigator sequences) can be evaluated during the sequencing, and the further course of the sequencing can be influenced by the results of this evaluation, wherein the time period between recording the data and influencing the further course is short in comparison with the typical time constants of the respiratory movement (in this case, particularly, the respiratory cycle of a human being, which amounts to between 3 and 10 seconds).

The main problem with the acceptance/rejection algorithm is that the respiration of the patient frequently varies during the examination. The variations in the respiratory movement can be, thereby, such that the respiratory positions within the once specified acceptance window are rarely, or no longer, detected. This leads to extended acquisition periods and can even lead to the measurement not being completed at all in the normal manner.

A large number of alternative prospective gating algorithms exist, which either attempt to improve the efficiency with respect to the acceptance/rejection algorithm, or to make the measurements more robust, for the case that the respiration during the measurement varies or drifts. Common to all of this is that—as long as the respiration is recorded with a navigator—the prospective decision is based solely on the last measured respiration position (e.g. the last measured diaphragm position or the last measured diaphragm positions).

The most important algorithm, by far, that addresses this problem is "Phase Ordering With Automatic Window Selection" (PAWS), which is described, for example, in the article by P. Jhooti, P. D. Gatehouse, J. Keegan, N. H. Bunce, A. M. Taylor, and D. N. Firmin, "Phase Ordering With Automatic Window Selection (PAWS): A Novel Motion-Resistant Technique for 3D Coronary Imaging," Magnetic Resonance in Medicine 43, Pages 470-480 (2000) and in the US patent, U.S. Pat. No. 7,039,451 B1. PAWS finds a final acceptance window during the runtime, and can thus react in a flexible manner to a changing respiration. A further goal of PAWS is to ensure a certain degree of "phase-encode ordering" (or in short, "phase ordering"). This means that adjacent lines in the k-space are acquired in similar respiration states. In particular, a variation in the respiratory state during acquisitions in the vicinity of the k-space center, which is particularly sensitive to movement, is to be avoided. PAWS was developed for a 3D Cartesian acquisition technique. The ky-kz array system used for this acquires a complete kx-kz plane of the 3-dimensional k-space following each navigator. The modulation of the k-space signal along the kz axis resulting from the transcendental state after interrupting the stationary steady state by the navigator (as well as potential activated preparation pulses, or the waiting for a further physiological signal, such as an EKG trigger) on the kx-kz plane, is therefore smooth. Discontinuations may arise in the ky axis as a result of residual movement, which can be manifested in the image as artifacts and blurring along the first phase encoding axis ky. This does not only apply when the segment border exists in the vicinity of the k-space center. Peristaltic movements, as well, which are not detected by the respiratory sensor, can lead to artifacts in the images.

PAWS exists in different so-called "bin" variations. In PAWS, the width of the final acceptance window is determined. The respiratory positions encompassed by this acceptance window are found automatically during the runtime, in contrast to acceptance/rejection algorithms. The filling of k-space occurs in clusters. A cluster (in the original work, the term "bin" is used instead of "cluster") is characterized by a respiratory position range, an acceptance range, and comprises all k-space lines that have already been measured, after which a respiratory position in the respiratory position range assigned to the cluster is measured. In the n-bin variation of PAWS a respiratory position range is covered by n successive clusters, the width of which range is the same as the acceptance window.

Furthermore, a starting position in the k-space is assigned to each cluster, wherein the number of different starting positions is n. Different starting positions are assigned to clusters with adjacent respiratory positions where n>1. As soon as a respiratory position assigned to a cluster is measured with the navigator, the measurement of a k-space line that has not yet been measured within said cluster is initiated. The decision regarding which k-space lines still to be measured are selected takes into consideration, as a whole, the already acquired k-space lines of adjacent clusters as well. By way of example, a still missing k-space line is selected such that an arbitrary group of n adjacent clusters is complete to the greatest degree possible, wherein the arbitrary group of n adjacent clusters contains the cluster to which the current measured respiratory position is assigned; i.e. the group of n adjacent clusters comprising the largest possible number of different k-space lines. As soon as an arbitrary group of n adjacent clusters comprises all of the k-space lines that are to be measured, the measurement is stopped, because the overall variation in the respiratory position is limited in these measurement data, thereby, to the acceptance window.

The n different starting points and clusters of the n-bin variation of PAWS normally result in n segments in the k-space. For this, each segment consists of adjacent k-space lines. The variations to the respiratory positions within a segment measured with the navigator correspond to the position range assigned to a cluster (in the original work, the term "bin size" is used), and thus one $n^{th}$ of the acquisition window. The variation to the respiratory position is greater over the course of the entire k-space, and has an upper limit as a result of the specified acceptance window. The lines belonging to the same segment are measured during similar respiratory states. Thus, the modulation of the signal changes with the respiration at the segment borders. As a result, position jumps occur at the segment borders. An aim of the different bin-variations of PAWS is to displace the segment borders away from the movement sensitive k-space center. Another aim is to obtain a greater degree of efficiency.

In the previously mentioned article by Jhooti et al., as well as in the follow-up work by P. Jhooti, P. Gatehouse J. Keegan, A. Stemmer, D. Firmin: "Phase ordering with Automatic Window Selection (PAWS) with Half Fourier for Increased Scan Efficiency and Image Quality;" Proc. Intl. Soc. Mag. Reson. Med. 11 (2004); Page 2146, the 1-bin, 2-bin, 3-bin, and 4-bin variations are compared with one another. The result of this comparison shows that the 1-bin and the 2-bin variations of PAWS are the most efficient, i.e. for a given width of the acceptance window, the measurements are completed most quickly. The 1-bin variation is discarded because it does not allow for "phase ordering," the 4-bin variation (and higher) is discarded due to lower efficiency. The 3-bin variation is less efficient than the 2-bin variation. The reason for this is the unidirectional growth direction of the cluster with starting positions at the left and right k-space edges. As soon as the gap between one of these peripheral clusters and the central cluster (with a starting position in the k-space center, and a bidirectional growth direction) is closed, then said clusters continue to grow until the gap between the other peripheral clusters and the central cluster is closed, as soon as a respiratory position is measured that is assigned to the first peripheral cluster. This normally leads to multiple k-space lines acquired at the cluster borders (segment borders). This problem does not exist with the 2-bin variation. In this variation, every second cluster grows in a unidirectional manner from the left-hand k-space edge, through the k-space center, toward the right-hand k-space edge, and the remaining clusters grow in a unidirectional manner from the right-hand k-space edge, through the k-space center, toward the left-hand k-space edge. The measurement is complete as soon as two adjacent clusters (with opposite growth directions) "meet." However, with a symmetrical scanning of the k-space, as is the case with the 2-bin variation, the cluster border frequently lies in the vicinity of the k-space center, which is particularly sensitive to movement, which may lead to strong image artifacts. The probability of cluster borders lying in the vicinity of the k-space center is substantially lower with the use of partial Fourier (i.e. an asymmetric scanning of the k-space).

Of practical relevance, therefore, are the so-called 2-bin and 3-bin versions of PAWS, wherein, with symmetrical scanning, the 3-bin variation is preferred, and with asymmetric scanning, the 2-bin variation is preferred. This analysis is based on a 2-bin variation, in which the starting position alternates between the left-hand and right-hand k-space edges of adjacent clusters. Accordingly, the clusters grow, respectively, from the starting positions assigned thereto, firstly toward the k-space center.

It should also be noted that in some works, only a single respiratory position is assigned to a cluster. The width of the final acceptance window then amounts to n times the resolution of the respiratory signal. In this alternative formulation, one obtains a flexible selection of the acceptance window in that one first enlarges the respiratory position measured with the sensor, such that the n adjacent resulting respiratory positions cover a respiratory range corresponding to the width of the acceptance window.

PAWS was originally developed for a ky-kz array system, with which, in each case after recording the respiratory signal, all k-space lines are acquired with a specific value of the second phase-encoding gradient (in the kz axis). Accordingly, the "phase-ordering" is also limited to a Cartesian k-space axis, which can lead to a higher occurrence of residual movement artifacts in this axis.

Another prospective gating algorithm, which addresses the problem of a varying respiration, is the Diminishing Variance Algorithm (DVA) (Todd S. Sachs, Craig H. Meyer, Pablo Irarrazabal, Bob S. Hu, Dwight G. Nishimura: "The Diminishing Variance Algorithm for Real-Time Reduction of Motion Artifacts in MRI;" MRM 34; Pages 412-422 (1995)). First, in an initial phase, the k-space that is to be acquired is completely recorded, without gating, and for each acquisition period, the displacement of the respiration position in relation to a reference position is measured with a navigator, and recorded. At the end of the initial phase, the most frequent respiratory position is determined using a histogram, and designated as the mode for the statistical distribution. The k-space data, the stored respiratory positions of which deviate the most from the mode, are then re-acquired together with the navigator, and the histogram (and thereby the mode) is updated. This re-acquisition of the k-space data, which in each case deviate the most from the current mode, is continued until all of the respiratory positions lie within an acceptance window of a given width, or a time limit has been reached.

SUMMARY OF THE INVENTION

An object of the invention is to provide a method, a magnetic resonance apparatus, and a data storage medium that can be read electronically, with which the actual variation to the respiratory position during the acquisition of the image data used for the reconstruction in relation to a given acceptance range is expanded to a lesser degree than with a corresponding method in the prior art.

According to one aspect, the invention relates to a method for the acquisition of a measurement data set of a respirating examination subject by means of a gating algorithm of magnetic resonance technology. The measurement data set is acquired through numerous individual measurements of different k-space segments. For each individual measurement a respiratory position and a respiratory phase is determined by means of navigator measurements, wherein it is decided, based on the respiratory position and the respiratory phase, whether the individual measurements will be recorded in a final data set from which an image data set is reconstructed.

The navigator measurements are carried out, in each case, prior to and following the acquisition of the individual measurements.

The basis for the present invention is the insight that it makes a significant difference whether a specific navigator measurement is measured during the inhalation or the exhalation. The reason that the respiratory phase, i.e. the phase of the respiratory cycle (inhalation or exhalation) has not yet been used with prospective respiratory gating is presumably of a technical nature. The time interval between successive navigator measurements is relatively long, because each navigator measurement, on the one hand, reduces the efficiency of the measurement, and on the other hand, interrupts the stability ("steady state") of the magnetization. At the same time, each navigator measurement is encumbered by noise, such that solely from the comparison of two successive navigator measurements, it is normally not possible to determine the momentary respiratory phase. This noise can be reduced by temporary means, or with digital filtering of the series of measured respiratory positions. Both means delay, however, the availability of the data and thus make a prospective decision impossible.

The present invention expands the most important prospective gating algorithms in that the decision of whether a specific measurement data point is to be referenced for the image reconstruction is a function of the respiratory position (e.g. the diaphragm position) and the respiratory phase, during which the respiratory position is measured. The respiratory phase is a binary state thereby (inhalation, exhalation), or a triplet (inhalation, exhalation, unknown).

Furthermore, an algorithm shall be made available, which enables the determination of the momentary respiratory phase, even when the scanning rate of the physiological respiratory movement is low, and each individual scanning point is encumbered by noise.

With the method according to the invention for the acquisition of a measurement data set of a respirating examination subject by means of magnetic resonance technology, the measurement data set is acquired by means of numerous individual measurements, wherein for each individual measurement, a respiratory position and a respiratory phase is determined, based on which it is decided whether the individual measurement is to be recorded in the final measurement data set from which an image data set is reconstructed.

In accordance with the invention, by taking into account not only the respiratory position, but also the respiratory phase, for which an individual measurement is acquired, the actual overall variation to the respiratory position can be significantly reduced in the final measurement data set in comparison to methods which only reference the respiratory position.

In the method according to the invention, a physiological data point is thus determined by means of not only a respiratory position, e.g. measured with the navigator, (e.g. a diaphragm position). Instead, a physiological data point is a pair, consisting of a respiratory position and a respiratory phase. The respiratory phase can assume, thereby, two different values (states) (inhalation or exhalation) or three different values (states) (inhalation, exhalation, or unknown). In contrast to the respiratory position, the respiratory phase is not determined from a single navigator measurement. The respiratory phase can, in particular, be determined by means of at least two measurements of the respiratory position, wherein the temporal spacing between the two successive measurements of the respiratory position is relatively small compared to the respiratory cycle. For example, the temporal spacing between two successive measurements of the respiratory position is roughly one eighth of the respiratory cycle or less in its magnitude.

The respiratory positions, and therefore the respiratory phases, can be determined by means of navigator measurements. In some embodiments, a determination of the respiratory positions and the respiratory phases is also possible by means of external sensors, such as, e.g. respiratory belts. The determination of the respiratory positions and respiratory phases by means of navigators eliminates, however, the need for the otherwise necessary additional external sensors, and the use thereof.

The respiratory phases can be classified with the values "inhalation" or "exhalation," in order to establish whether a patient to be examined is currently inhaling or exhaling during the acquisition of the measurement data. If neither of the two values, "inhalation" or "exhalation" can be assigned thereto, then the respiratory phase can be classified with the value "unknown." Measurement data that have been acquired during an "unknown" respiratory phase can be discarded.

In accordance with one embodiment, the respiratory position and the respiratory phases of the examination subject can be separated into numerous predefined clusters, which each cover a predefined respiratory range of respiratory positions and respiratory phases. The measurement data set can be acquired through numerous shots, which each acquire a given number of k-space lines along a given three-dimensional k-space trajectory. Different shots can acquire different k-space lines, such that by means of the numerous shots, a predefined k-space region is scanned. The shots can each be assigned to a shot index, which is indicative of a sensitivity with respect to movement of the examination subject. The assignment of the shot indices to the shots can be such that adjacent shot indices are assigned to those shots that exhibit an incrementally different sensitivity with respect to movement. The method can include: A) measurement of the respiratory position and the respiratory phase of the examination subject by means of navigator technology, and B) Selection of a specific cluster, lying in the covered respiratory range of the measured respiratory position and respiratory phase. The method can furthermore include: C) Selection of a shot that is to be acquired as the shot exhibiting a shot index assigned thereto, which borders on a shot index of the last acquired shot for the specific cluster. The method can furthermore include: D) Acquisition of the shots that are to be acquired, and assignment of the shots to the specific cluster. The method can furthermore comprise: Execution of the steps A)-D) until at least two bordering clusters, which cover adjacent respiratory ranges of the examination subject, having the same respiratory phases, are collectively assigned to all of the shots of the measurement data set. The method can furthermore comprise the determination of an MR image from the shots assigned to the two bordering clusters.

The k-space lines can also be referred to as "views."

In the case discussed here, the respiratory phase can be defined, in particular with respect to "exhalation" and "inhalation," i.e. with two possible values. E.g. clusters corresponding to a maximum respiratory position (e.g. complete inhalation or complete exhalation) can also have an adjacent cluster with a different respiratory phase.

By the selection of the shots to be acquired for each cluster in this manner, which selects the respective bordering shot indices for acquisition, it is possible for the cluster to be filled systematically, and classified with respect to an incrementally different sensitivity with respect to movement. For example, the filling of the various clusters can occur such that first, those shots having a greater degree of sensitivity to movement (lesser degree of sensitivity to movement) are acquired, and then those shots having an increasingly lower degree of sensitivity to movement (increasingly greater degree of sensitivity to movement) are systematically acquired and classified.

By assigning the shot indices to the shots, such that bordering shot indices indicate an incrementally different sensitivity to movement, it is possible to obtain the following: The shot indices are assigned to the shots in a logical manner. For example, the shots can first be sorted with respect to their sensitivity to movement, and then these sorted shots can be assigned to the shot indices in, e.g. a continuous, or in an increasing, or in a decreasing manner.

As an example, the predefined clusters can be grouped such that the entire respiratory range of respiratory positions of the examination subject is covered without gaps. In this manner, it can be possible to select a specific cluster in step B) of the method described above, in which the measure respiratory position lies within the covered respiratory range thereof.

As an example, those shots, which acquire one or more k-space lines having a comparably small spacing to a k-space center, can exhibit a comparably high degree of sensitivity to movement. Accordingly, those shots which acquire no, or only a small number of, k-space lines in the vicinity of the k-space center, can exhibit a comparably low degree of sensitivity to movement on the part of the examination subject. By the assignment of the shot indices in this manner, such that they are indicative of this sensitivity to movement, it is possible to obtain that the selection and acquisition of the shots, taking into consideration the sensitivity to movement is executed, and can, e.g. be optimized in this respect.

It is possible, for example, to obtain an optimization of the acquisition of the shots with respect to sensitivity to movement by means of correlated selection and acquisition of shots between adjacent clusters. It may be unnecessary to acquire shots, which are acquired for one of the adjacent clusters, for the other adjacent cluster. This may be the case because the MR image can be determined from the at least two bordering clusters, with which the shot indices are selected for the correlation.

A cluster may exhibit more than one neighbor, e.g. it may exhibit two neighbors. The following observations can, for example, apply to any arbitrary neighbor.

As an example, for one of the first of two adjacent clusters, which cover adjacent respiratory ranges of the examination subject, first those shots can be selected and acquired, which exhibit assigned shot indices that correspond to a greater degree of sensitivity to movement. For a second of the two adjacent clusters, first those shots can be selected and acquired, which exhibit assigned shot indices corresponding to a lower degree of sensitivity to movement.

Thus, in other words, it is possible for the selection of the shot to be acquired for the first of the two adjacent clusters, to comprise: selection of that shot which has not yet been measured for the first of the two bordering clusters, and exhibits the greatest degree of sensitivity to movement, of these not yet measured shots. For the second of the two bordering clusters, the selection of the shot that is to be acquired can comprise: selection of that shot, which has not yet been measured for the second of the two bordering clusters, and exhibits the lowest degree of sensitivity to movement, of these not yet measured shots.

Various techniques are possible for the concrete selection of the various shot indices. For example, continuously increasing shot indices can indicate a continuously increasing or decreasing sensitivity of the respective shots to movement on the part of the examination subject. Other variations to the selection of the shot indices are, however, also possible, e.g. under the additional consideration of a k-space component of the respective k-space trajectory.

The selection of a shot that is to be acquired can furthermore occur such that the k-space region is scanned, to the greatest degree possible, in a uniform manner along various axes and/or on different sides of the k-space region.

In the above, techniques are described which primarily concern the selection and acquisition of specific shots based on the shot indices for a predefined quantity of shots. However, it is also possible to determine the number of shots oneself according to various embodiments. In particular, the shots, or the shot indices, respectively, can be determined such that they exhibit the characteristic sensitivity to movement. This can take place, e.g. by means of the subdividing the k-space region into sectors exhibiting a well-defined spacing to the k-space center. This spacing can be indicative of the sensitivity to movement of a specific acquired k-space line.

The k-space lines or views can be disposed along a phase encoding gradient field axis, wherein the k-space trajectories, or views, respectively, of numerous shots, are disposed in a substantially radial manner in a plane, which is oriented such that it is perpendicular to the phase encoding gradient field axis.

Substantially radially can mean that the k-space trajectories or views of the various shots also exhibit a tangential component, which can be, however, relatively small compared to its radial component.

It is possible that the k-space region is subdivided into sectors, which are defined with respect to their spacing to a k-space center, wherein, for each of the numerous shots, in each case there is a k-space line located in each sector.

For example, the k-space trajectory can scan, for each shot, different k-space lines in a series, which corresponds to the neighborhood of the sectors in which the various k-space lines are located.

A magnetic resonance apparatus according to the invention comprises a base field magnet, a gradient field system, a radio-frequency antenna, and a control device for controlling the gradient field system and the radio-frequency antenna, and an image processor for receiving the measurement signals recorded by the radio-frequency antenna, for the evaluation of the measurement signals and for creating magnetic resonance images, and is equipped to execute the described method.

The invention also encompasses a non-transitory data storage medium that can be read electronically on which control data are stored that can be read electronically, which are designed to cause the described method to be executed when the data storage medium is loaded in a control device of a magnetic resonance apparatus.

The advantages and designs presented in reference to the method apply analogously to the magnetic resonance apparatus and the data storage medium.

BRIEF DESCRIPTION OF THE DRAWINGS

FIG. 10 shows an embodiment of a method according to the invention, in conjunction with the new optimized 2-bin PAWS.

FIG. 11 shows an example of a measured respiratory signal.

DESCRIPTION OF THE PREFERRED EMBODIMENTS

Figure 1:
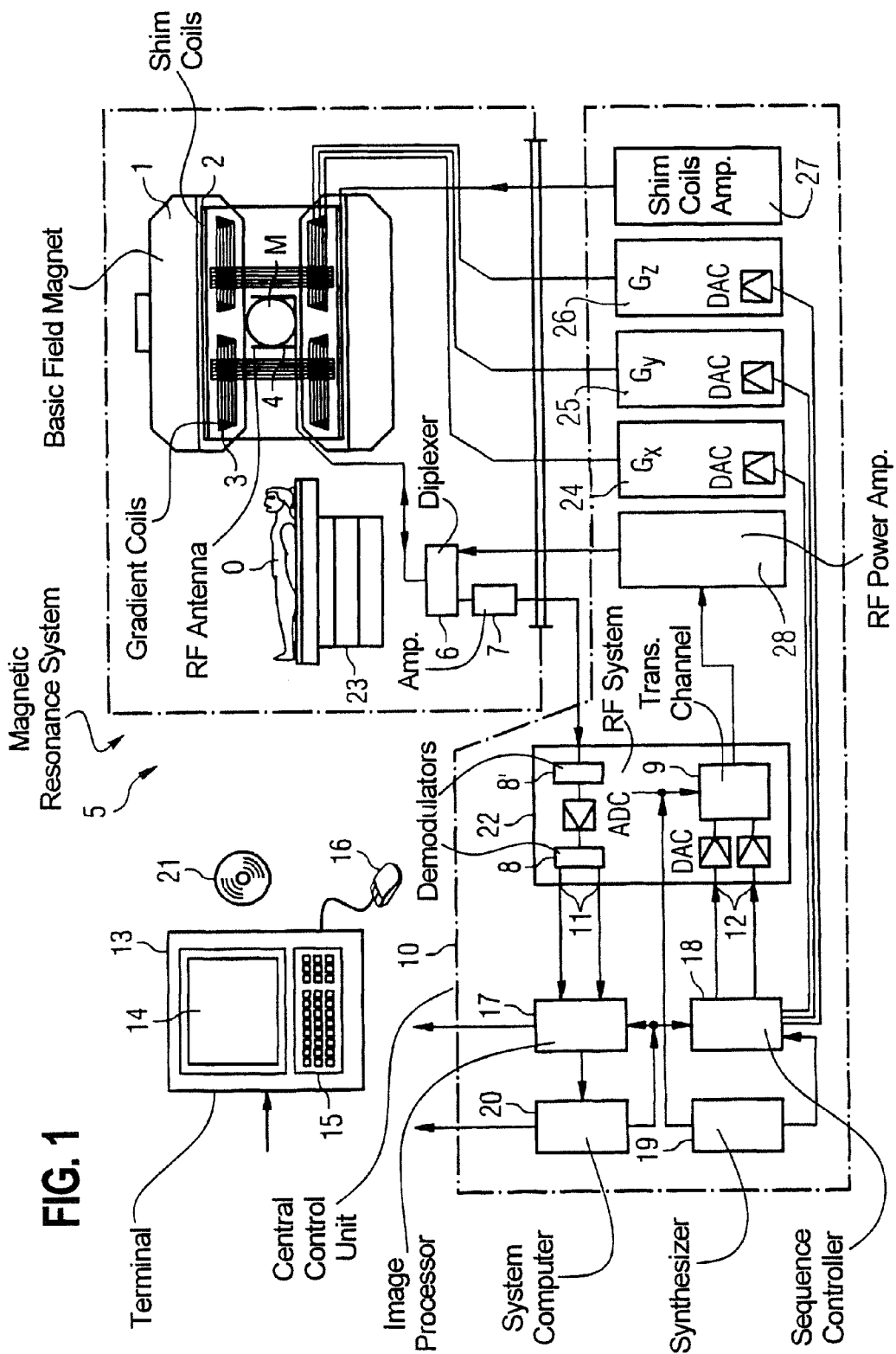
FIG. 1 schematically illustrates a magnetic resonance apparatus according to the invention.

FIG. 1 schematically illustrates a magnetic resonance apparatus 5 (a magnetic resonance imaging or tomography device). A basic field magnet 1 generates, a temporally constant strong magnetic field for the polarization or alignment of the nuclear spin in a region of an examination subject O, such as a portion of a human body that is to be examined, lying on a table 23 in order to be moved into the magnetic resonance apparatus 5. The high degree of homogeneity in the basic magnetic field necessary for the magnetic resonance measurement (data acquisition) is defined in a typically sphere-shaped measurement volume M, in which the portion of the human body that is to be examined is placed. In order to support the homogeneity requirements temporally constant effects are eliminated by shim-plates made of ferromagnetic materials are placed at appropriate positions. Temporally variable effects are eliminated by shim-coils 2 and an appropriate control unit 27 for the shim-coils 2.

A cylindrically shaped gradient coil system 3 is incorporated in the basic field magnets 1, composed of three windings. Each winding is supplied by a corresponding amplifier 24-26 with power for generating a linear gradient field in a respective axis of a Cartesian coordinate system. The first partial winding of the gradient field system 3 generates a gradient $G_x$ in the x-axis, the second partial winding generates a gradient $G_y$ in the y-axis, and the third partial winding generates a gradient $G_z$ in the z-axis. Each amplifier 24-26 has a digital-analog converter (DAC), controlled by a sequencer 18 for the accurately-times generation of gradient pulses.

A radio-frequency antenna 4 is located within the gradient field system 3, which converts the radio-frequency pulses provided by a radio-frequency power amplifier into a magnetic alternating field for the excitation of the nucleii by tipping ("flipping") the spins in the subject or the region thereof to be examined, from the alignment produced by the basic magnetic field. The radio-frequency antenna 4 is composed of one or more RF transmitting coils and one or more HF receiving coils in the form of an annular, linear or matrix type configuration of coils. The alternating field based on the precessing nuclear spin, i.e. the nuclear spin echo signal normally produced from a pulse sequence composed of one or more radio-frequency pulses and one or more gradient pulses, is also converted by the RF receiving coils of the radio-frequency antenna 4 into a voltage (measurement signal), which is transmitted to a radio-frequency system 22 via an amplifier 7 of a radio-frequency receiver channel 8, 8'. The radio-frequency system 22 furthermore has a transmitting channel 9, in which the radio-frequency pulses for the excitation of the magnetic nuclear resonance are generated. For this purpose, the respective radio-frequency pulses are digitally depicted in the sequencer 18 as a series of complex numbers, based on a given pulse sequence provided by the system computer 20. This number series is sent via an input 12, in each case, as real and imaginary number components to a digital-analog converter (DAC) in the radio-frequency system 22 and from there to the transmitting channel 9. The pulse sequences are modulated in the transmitting channel 9 to a radio-frequency carrier signal, the base frequency of which corresponds to the resonance frequency of the nuclear spin in the measurement volume. The modulated pulse sequences of the HF transmitter coil are transmitted to the radio-frequency antenna 4 via an amplifier 28.

Switching from transmitting to receiving operation occurs via a transmission-receiving switch 6. The RF transmitting coil of the radio-frequency antenna 4 radiates the radio-frequency pulse for the excitation of the nuclear spin in the measurement volume M and scans the resulting echo signals via the HF receiving coils. The corresponding magnetic resonance signals obtained thereby are demodulated to an intermediate frequency in a phase sensitive manner in a first demodulator 8' of the receiving channel of the radio-frequency system 22, and digitalized in an analog-digital converter (ADC). This signal is then demodulated to the base frequency. The demodulation to the base frequency and the separation into real and imaginary parts occurs after digitization in the spatial domain in a second demodulator 8, which emits the demodulated data via outputs 11 to an image processor 17. In an image processor 17, an MR image is reconstructed from the measurement data obtained in this manner through the use of the method according to the invention, that includes computation of at least one disturbance matrix and the inversion thereof, in the image processor 17. The management of the measurement data, the image data, and the control program occurs via the system computer 20. The sequencer 18 controls the generation of the desired pulse sequences and the corresponding scanning of k-space with control programs, in particular, in accordance with the method according to the invention. The sequencer 18 controls accurately-timed switching (activation) of the gradients, the transmission of the radio-frequency pulse with a defined phase amplitude, and the reception of the magnetic resonance signals. The time base for the radio-frequency system 22 and the sequencer 18 is provided by a synthesizer 19. The selection of appropriate control programs for the generation of an MR image, which are stored, for example, on a DVD 21, as well as other user inputs such as a desired number n of adjacent clusters, which are to collectively cover the desired k-space, and the display of the generated MR images, occurs via a terminal 13, which includes units for enabling input entries, such as, e.g. a keyboard 15, and/or a mouse 16, and a unit for enabling a display, such as, e.g. a display screen.

Figure 2:
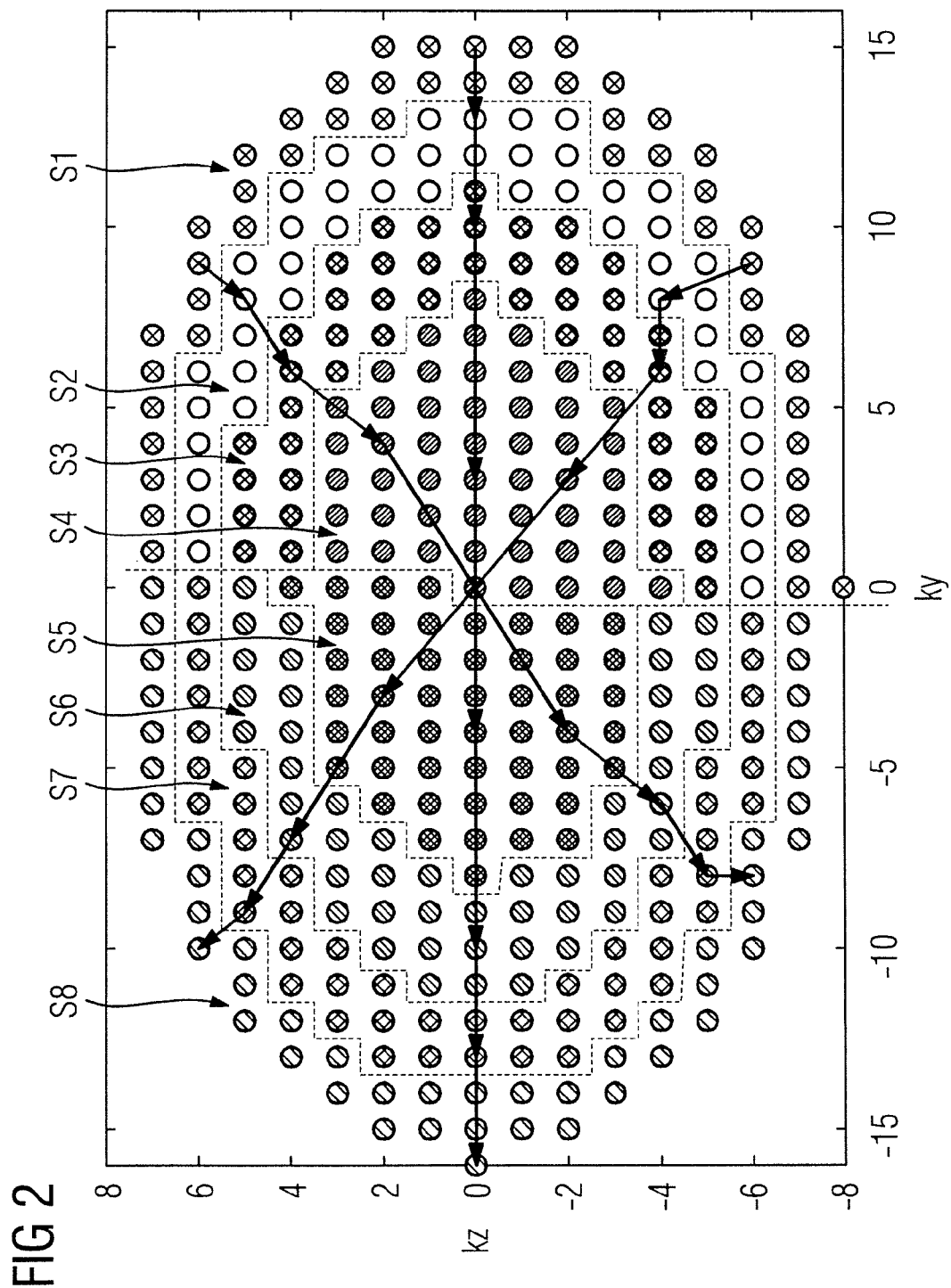
FIG. 2 shows an example of a new allocation of views to sectors and shots.

FIG. 2 shows an example of a new k-space array system. A kz-ky plane is shown, in which views (depicted by circles filled with various patterns) are disposed in a Cartesian manner.

Figure 3:
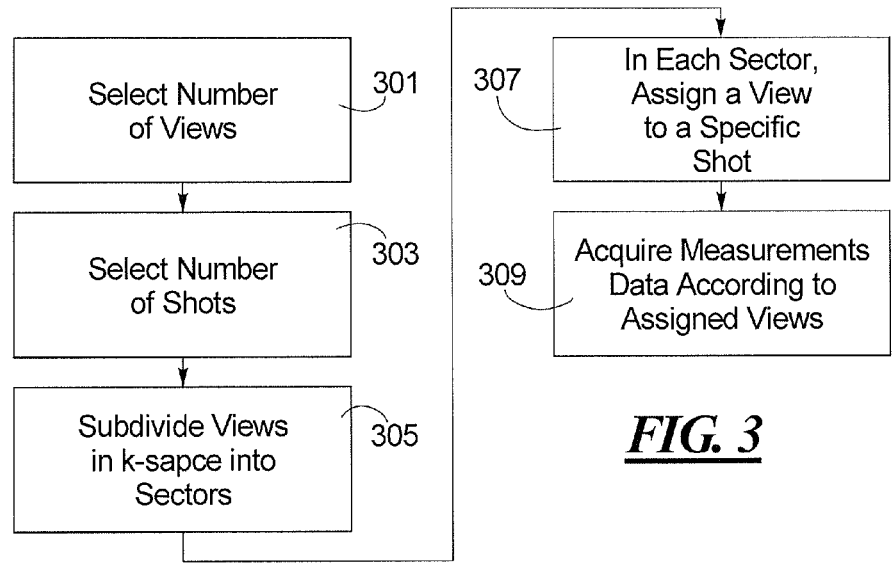
FIG. 3 is a flow chart for a new array of the k-space to be scanned in sectors and shots.

FIG. 3 shows a flow chart for arranging the k-space that is to be scanned in sectors and shots.

For this purpose, first a number Nv of views, which are to be acquired for each shot, is selected (block 301). This occurs, for example, by means of an input by a user at a terminal 13 of a magnetic resonance apparatus 5. The selection of the views per shot can be freely selected with, for example, the use of a navigator for determining the respiratory signal as a physiological signal, as well as the temporal resolution of the respiratory signal, because after a navigator, a shot with the selected number of views is acquired. From the total number of the views to be measured, (which is determined by means of, among other factors, the resolution, which has, in turn, been selected by the user) and the number Nv of views per shot is therefore established by the number Ns of shots which are required in order to fully scan the k-space that is to be scanned (block 303).

The views in the k-space are subdivided into sectors S1, S2, S3, S4, S5, S6, S7, S8 (block 305). Views which are assigned to the same sector are each filled with the same pattern. In addition, the borders of the sectors S1, S2, S3, S4, S5, S6, S7, S8 are indicated by thin broken lines.

The number of different sectors is the same as the number of views per shot, and, e.g. a user-defined parameter. In the depicted example, the number of sectors and the views per shot equals eight.

The number of views per sector is the same as the number of shots Ns. In the example, the number of views in each sector, and therefore the number of shots, equals 49. Views which are assigned to the same sector have a similar spacing from the k-space center, and are located in the same hemisphere (in the example in FIG. 2, the first hemisphere is defined by ky>0, or (ky=0 and kz≤0)). Advantages derived therefrom are obtained with an asymmetric recording of the k-space (partial Fourier).

Each shot acquires, thus, one view per sector. For this, views of a specific sector are acquired at the same point in time after the navigator sequence, or after the starting of the shots, respectively.

All views are assigned to a shot, wherein in each sector a view is assigned to a specific shot (block 307). The assignment of the individual views of a sector to a specific shot occurs in accordance with their orientation in the kz-ky plane, for example, in accordance with their azimuth angle in a polar coordinate system. This array results in a smooth modulation of the k-space (resulting from the transcendental state after an interruption of the stationary steady state) along the quasi-radial scanning direction.

As an example, three shots are depicted in FIG. 2 by means of thick series of arrows. With the acquisition of measurement data, the views assigned to the same sector and to different shots each assume the same position within the shots (block 309). As one sees in the example in FIG. 2, the sequence for the acquired views for each shot corresponds respectively to the sectors thereof, which, in the depicted case, are from S1 to S2 to S3 to S4 to S5 to S6 to S7 to S8. The shots thus proceed in quasi-radial k-space trajectories, in this case from the right edge to the left edge of the k-space that is to be scanned.

The array system has the advantage, in comparison with the array system previously used in conjunction with the PAWS technique, that it is less susceptible to ghost artifacts resulting from residual movement, because these are smeared at the azimuth. Furthermore, the array allows for a free selection of the views per shot, and therefore the temporal resolution of the physiological respiratory signal recorded with the navigator sequence. Furthermore, it is compatible with so-called elliptical scanning, in which the views in the peripheral corners of the k-space, particularly in the ky-kz plane, having a relatively low information content, are not acquired, in favor of a shorter measurement time period, as is also the case in the depicted example. Furthermore, the intended distribution of the k-space sectors is compatible with a varying density of the k-space scanning, as is the case, for example, with parallel imaging with auto-calibration.

The generalized PAWS description enables the array system described above to be implemented together with PAWS, in that the shots, as already mentioned above, are assigned a shot index for the views distributed in the sectors, which fulfills the suppositions c) and d) given above.

For this, the following approach can be used:

First, each shot exhibits an azimuth angle φ e.g. between [−π, π]. For this, one can, e.g., use the average azimuth angle of the views per shot (arctan 2 (ky, kz)) in the first hemisphere, or the azimuth angle of the views in one of the sectors, advantageously one of the sectors lying in the vicinity of the k-space center, such as the sector S4 in FIG. 2. This azimuth angle is a suitable scalar, and therefore array criteria, for the shots, which describes a neighborhood of the shots. It is important that one realizes that it is not necessary for the allocation shot→scalar to be reversible. The shot index ns0 is set advantageously to be equal to the shot index of the shots acquiring the k-space center. In the example in FIG. 2, this shot has an azimuth angle φ=0, and thus lies in the center of the evaluation range of ns [0, Ns−1].

In a truly radial trajectory, all shots have the same degree of sensitivity to movement. Nevertheless, one can still use the generalized PAWS description. The selection of the ns0 is then free.

Figure 5:
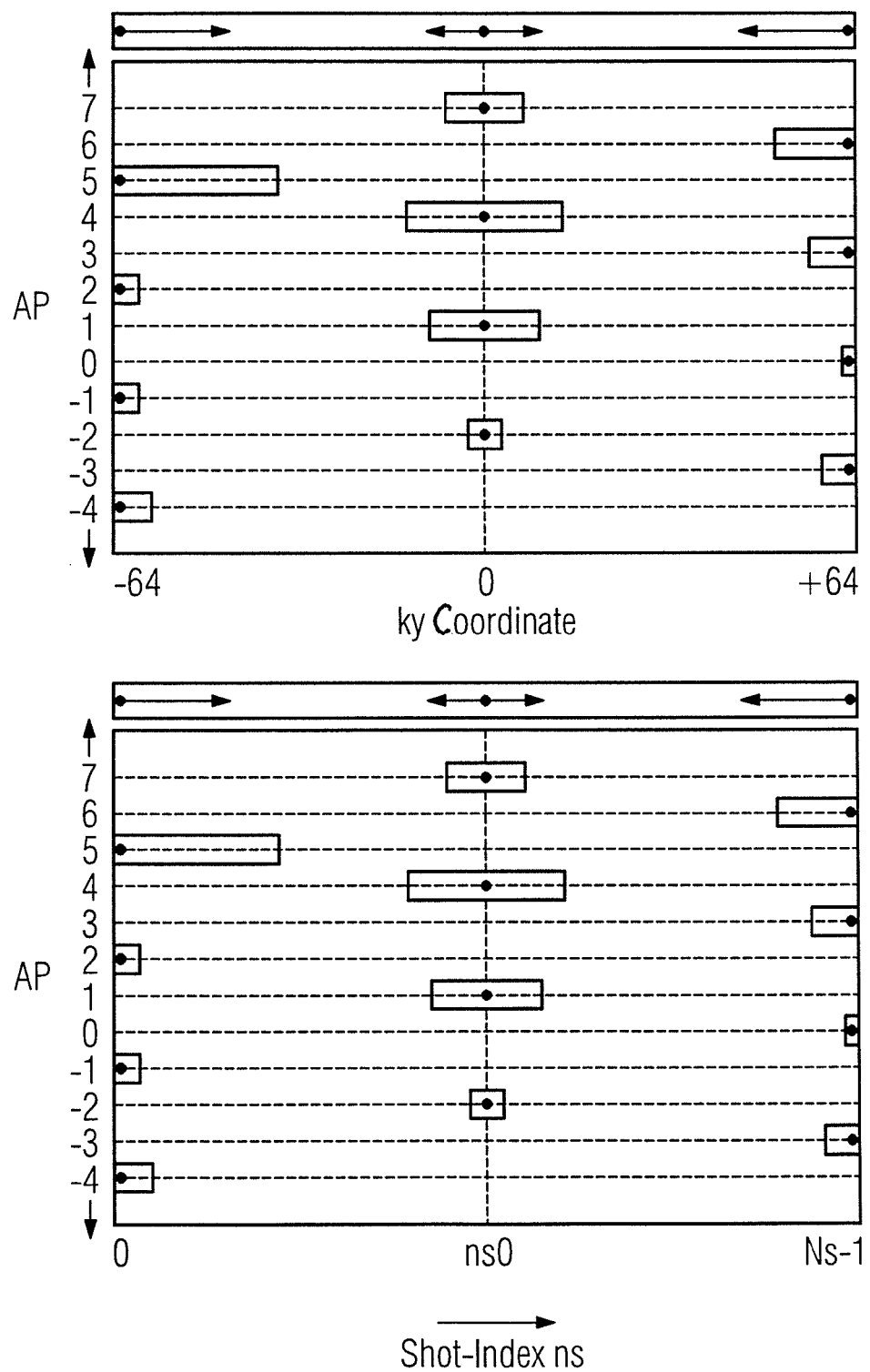
FIG. 5 is an example of a comparison of the PAWS array system of the original work using on the ky-coordinate with a new array system according to the shot index for a 3-bin PAWS algorithm.

With the determination by means of the above suppositions a)-d), one can thus use the PAWS algorithm on arbitrary 2-dimensional Cartesian ky-kz array systems and k-space trajectories, in that one replaces the ky coordinates of the original work (Jhooti et al.) with the shot index ns. This is simply done, in that a cluster ("bin" in the original work) is assigned a starting position at the left-hand k-space edge (kymin in the original work) of the shot index ns=0 as the starting position, and a cluster with a starting position on the right-hand k-space edge (kymax in the original work) is assigned the shot index ns=Ns−1 as the starting position, and a cluster having the starting position in the k-space center (in the original work) is assigned the shot index ns=ns0, with a maximum movement sensitivity, as the starting position. In FIG. 5, an example of a transformation of this type is depicted, from the array system of the original work using the ky coordinate (above) to an array system in accordance with the shot index for a 3-bin PAWS algorithm (below). In the vertical column, the respiratory position AP is recorded for each case.

Figure 4:
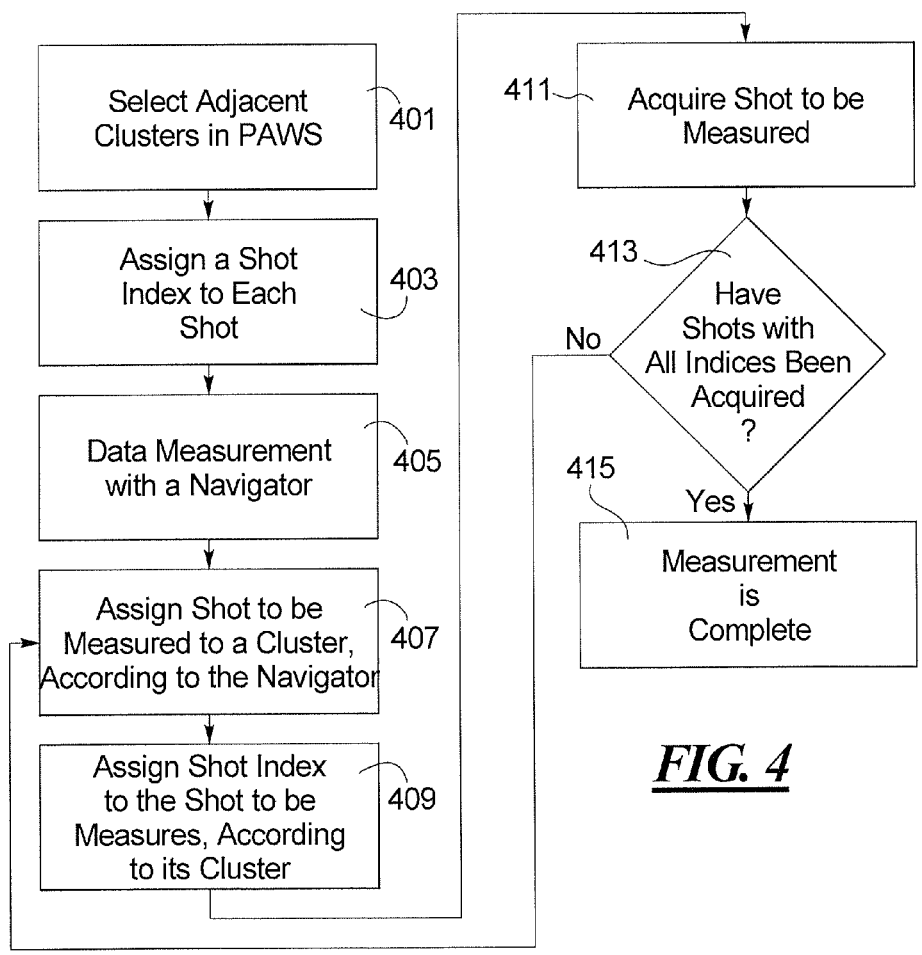
FIG. 4 is a flow chart of a new PAWS method.

A flow chart for a generalized PAWS method is depicted in FIG. 4.

For this, first, as is normal with PAWS, the number n is selected, which indicates the number of adjacent clusters that should, collectively, completely fill the k-space, in order to obtain a complete measurement data set, which does not exceed a given overall variation to the respiratory position during the measurements (block 401).

Each of the Ns shots is assigned a shot index ns∈[0; . . . ; ns0; . . . ; Ns−1] (block 403), as described above, wherein the assignment occurs such that the shot indices ns are arranged such that the sensitivity of the shots with respect to movement by the examination subject increases from shot index ns=0 up to shot index ns=ns0, and in turn, decreases from shot index ns=ns0 to shot index ns=Ns−1.

The measurement is initiated with a navigator measurement for determining a respiratory signal and therefore a momentary respiratory position (block 405).

For this purpose, the shot that is to be measured after the navigator measurement is assigned to a cluster, in the PAWS method, in a typical manner, corresponding to the respiratory signal measured with the navigator measurement (block 407).

After it has been determined by the navigator measurement, to which cluster the following shot that is to be measured is assigned, a shot index is determined for the shot to be measured, in relation to the already acquired shot indices for the previously selected cluster and its adjacent clusters (block 409). If no shot has yet been acquired in the cluster to which the measured shot is to be assigned, the shot having the shot index corresponding to the starting position assigned to said cluster is selected (block 409).

The corresponding shot with the selected shot index is acquired as the shot that is to be measured (block 411).

If, after the last acquisition of a shot, in a given number n of adjacent clusters, all of the shots with all of the Ns shot indices have been acquired (query 413) then the measurement is complete (block 415).

Accordingly, with the generalized PAWS method as well, a so-called peripheral cluster having a starting position 0 grows toward the k-space center, in that it selects the next, not yet acquired, larger shot index, and a peripheral cluster having a starting position Ns−1 grows in that it selects the next smaller, not yet acquired shot index.

The central cluster (having the starting position ns0) selects from the n possible cluster combinations the cluster that is complete to the greatest extent, i.e. the cluster already comprising the most shots having different shot indices, and then grows toward a smaller, or larger, respectively, shot index, depending on whether the quantity formed by shots having ns≤ns0, or, respectively, the quantity formed by shots having ns≥ns0, which are not yet acquired from the cluster combination, has more elements. As soon as an arbitrary group of n adjacent clusters comprises all of the shot indices [0, . . . , Ns−1] that are to be measured, the measurement is complete (block 415), because the overall variation in the respiratory position is thus limited to the acceptance window. If there are still cluster combinations of n adjacent clusters shots in which not all Ns shot indices are comprised, then at block 405, the method is continued, and a new navigator measurement is acquired, in each case, with a new subsequent shot.

In the example in FIG. 2, adjacent views in the k-space each belong to shots with a similar azimuth angle, and thus to shots with adjacent shot indices. By this means, the generalized PAWS algorithm ensures that adjacent views are acquired during similar respiratory states. In the example in FIG. 2, the shot that acquires the k-space center has the azimuth angle φ=0, and thus lies in the center of the evaluation range of the shot indices. One can thus assume that the results contained in the original work (with regard to efficiency and remaining susceptibility to movement) can also be directly applied to the proposed, more flexible, ky-kz array system. With the described method, the PAWS concept can be used with any arbitrary ky-kz array system and with any arbitrary non-Cartesian k-space trajectories.

With the use of a navigator for recording the movement, the stationary steady state of the magnetization is interrupted by the execution of the navigator sequence. With the array system according to the original work from Jhooti et al., this interruption occurs, in each case, after the acquisition of Nz TR intervals, wherein Nz is the number of phase encoding steps in the second phase encoding direction. The temporal resolution of the respiratory signal is thus linked directly to the spatial resolution of the imaging sequence along the second phase encoding direction. However, the respiratory signal measured with the navigator is only valid for a limited period of time, which is short in relation to the respiratory interval. This means that the array system used in the original work by Jhooti et al. inherently limits the maximum resolution in one of the two Cartesian axes. With the use of the proposed, generalized PAWS algorithm, having an array system such as that described, in particular, in reference to FIG. 2, a limitation of this type does not exist, because the number of views per shot, and thus the temporal resolution of the respiratory signal, can be freely selected. This advantage is particularly important, because the goal of respiratory gated measurements is frequently to avoid the inherent resolution limitation to measurements made while holding one's breath, resulting from the limited ability of the patient to hold its breath for longer periods of time.

The problem of the limited temporal validity of the navigator signal can be avoided in part through the use of a 1-dimensional centric array system along the kz axis. An array system of this type starts in the k-space center, and acquires alternating views with positive and negative values for kz, in such a manner that the absolute moment of the phase encoding steps grows in a continuous manner. This centric array system has, however, the disadvantage that it can lead to artifacts resulting from turbulences as a result of the larger phase encoding jumps between the TR intervals.

As an alternative to the normal n-bin PAWS method, in the following an optimized 2-bin PAWS method shall be presented.

Figure 6:
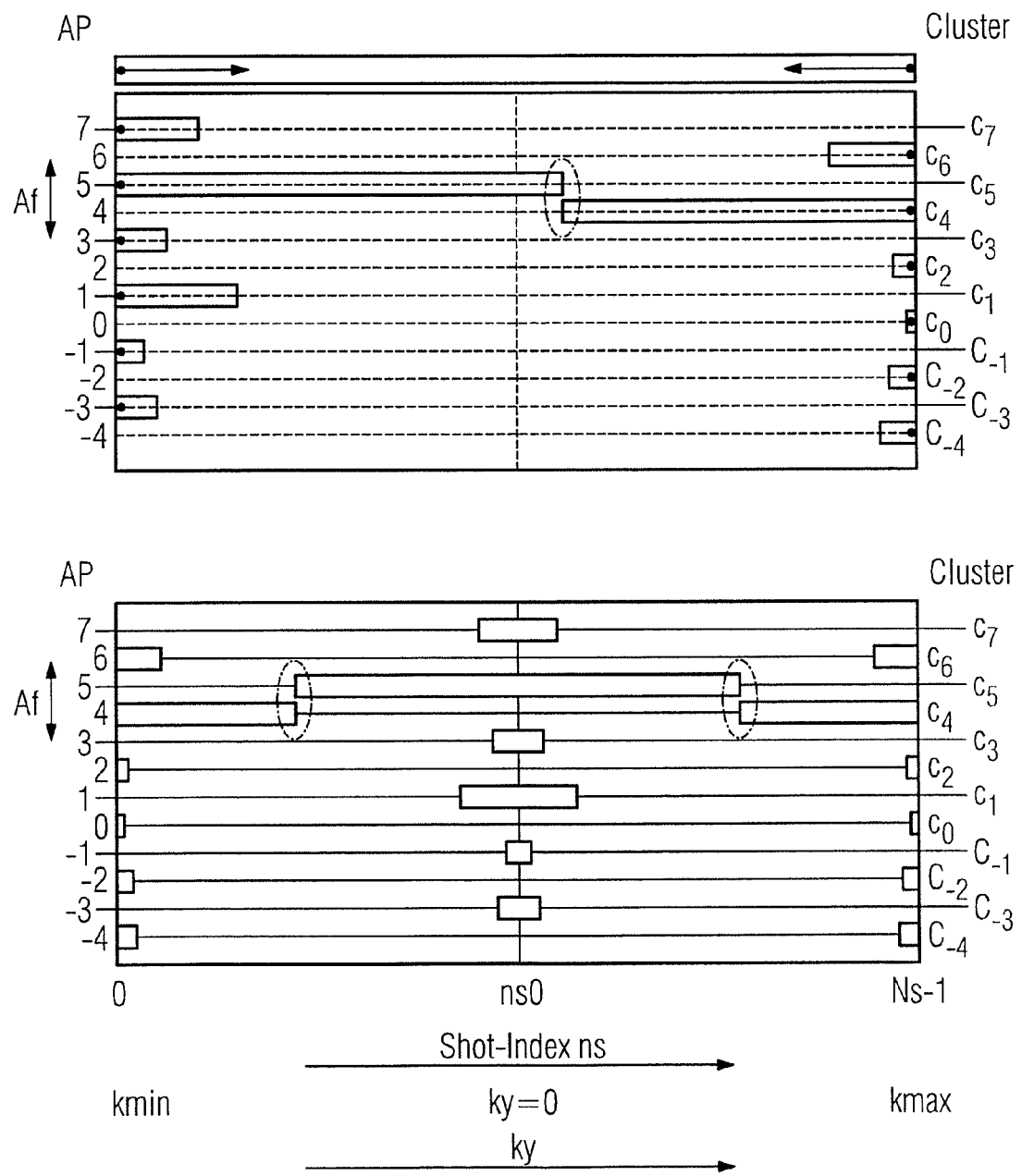
FIG. 6 is an example of a comparison of the previous 2-bin PAWS with a new optimized 2-bin PAWS.

FIG. 6 shows, by way of example, a comparison of the previous 2-bin PAWS with a new, optimized 2-bin PAWS, wherein a prior 2-bin PAWS is depicted at the top, and the new 2-bin PAWS is depicted below.

As is described in the original work (Jhooti et al.), in the original 2-bin PAWS variation the starting position of adjacent clusters alternates between the left-hand and the right-hand k-space edge. In the upper part of FIG. 6, clusters having an even-numbered index are assigned the right-hand starting position, and clusters with an odd-numbered index are assigned the left-hand starting position. This corresponds in the generalized depiction, described herein, to an alternation between ns=0 and ns=Ns−1. Accordingly, a cluster with the starting position ns=0 grows, in that it selects the smallest shot index that has not yet been acquired from the cluster. A cluster with a starting position ns=Ns−1 grows in that it selects the largest shot index that has not yet been acquired from the cluster. In the following, a shot index ns shall always be referred to, even if the original array can be used in accordance with the ky coordinates. The width of the respiration position range assigned to each cluster normally corresponds to half of the acceptance window (AF). The measurement is complete as soon as two arbitrary adjacent clusters have collectively acquired all shots. This is the case in the example in FIG. 6 for the clusters c4 and c5. In terms of imaging, a cluster "growing from the left side" (starting position ns=0) and one of the two adjacent clusters "growing from the right side" (starting position ns=Ns−1) meet, such that both clusters, collectively, span the overall value range [0, . . . , Ns−1]. To the extent that these two clusters comprise nearly the same number of shots, frequently a cluster border (marked with an oval drawn with a broken line in FIG. 6.) is then obtained in this connection in the movement sensitive region surrounding the k-space center.

In the optimal 2-bin PAWS implementation presented here, two cluster types also alternate. The one cluster type has the shot having the maximum movement sensitivity ns=ns0 as the starting position and shall be referred to in the following as the central cluster. The other cluster type does not have a clear starting position, and shall be referred to in the following as a peripheral cluster. In the example in FIG. 6, clusters with an odd-numbered index are central clusters, and clusters with an even-numbered index are peripheral clusters. The starting position of a peripheral cluster is either ns=0, or ns=Ns−1, or, respectively, either the right-hand or the left-hand k-space edge in the ky coordinates, wherein the actual starting position is first decided on during the runtime. A peripheral cluster grows, independently of its starting position, either from the largest shot index not yet belonging to the cluster, downward toward ns0, or ky=0, respectively, or from the smallest shot index not yet belonging to the cluster, upward toward ns0 or, ky=0, respectively. The decision as to which direction of growth shall currently be preferred, occurs in turn during the runtime. This is schematically depicted in a flow chart in FIG. 7.

If, as has already been described above, a respiratory position is measured by means of a navigator measurement (block 701, corresponding to block 405 in FIG. 4), which lies in the respiratory position range of a peripheral cluster cn, in accordance with the normal array used in PAWS (block 703, corresponding to block 407 in FIG. 4), then it is next queried whether the cluster combination cn–c(n−1) or cn–c(n+1) is closer to completion (blocks 705 and 707). For this purpose, the shots already acquired in the clusters cn–c(n−1) and cn–c(n+1) are first counted, and these are stored with the respective number M− or M+(block 705). The adjacent cluster cx, which, together with the peripheral cluster cn, is closest to completion, is selected according to these numbers M− or M+, wherein the cluster c(n−1) is selected if M+ is greater than M−. The clusters are labeled in the normal fashion, corresponding to their respiratory position range (cluster cn corresponds to the $n^{th}$ respiratory position). Accordingly, c(n−1) and c(n+1) are central clusters, and the next two neighbors thereof are peripheral clusters cn. In this manner, the cluster c(n−1) is selected if the cluster combination cn–c(n−1) is closer to completion, and otherwise, the cluster c(n+1) is selected.

Next, the number of shots Mlow, having an index in the range [0, ..., ns], which have not yet been acquired from the two clusters (cn and the selected cx), and the number of shots Mhigh, having an index in the range [ns, ..., Ns−1], which have not yet been acquired from the two clusters, are counted (block 709). If the cluster cn, which is assigned to the last measured respiratory position, as in the given case, is a peripheral cluster ("y" in query 711), then the peripheral cluster cn grows from its smallest not yet acquired shot index toward ns0, or ky=0, respectively, if Mlow is greater than Mhigh ("y" in query 713), in which the smallest, not yet acquired, shot index is acquired (block 715); otherwise, it grows from its largest not yet acquired shot index toward ns0, or ky=0, respectively ("n" in query 713), in which the largest, not yet acquired shot index, is acquired (block 715).

A peripheral cluster spans, therefore, in general, two contiguous index ranges. The one starts at the smallest shot index ns=0 (or the left-hand k-space edge), and grows toward larger shot indices. The other starts at the largest shot index ns=Ns−1 (or the right-hand k-space edge), and grows toward smaller shot indices. Alternatively, one can also refer to the index range for peripheral clusters being continued at the range borders in a periodic or cyclical manner.

The decision process runs in a similar manner, when the last measured respiratory position lies in the respiratory position range of a central cluster cn.

As explained above, it is checked to see which of the cluster combinations, cn–c(n−1) and cn–c(n+1), is closer to completion, and this cluster combination is selected (blocks 705 and 707). Next, the number of shots Mlow, having an index in the range [0, ns], which are not yet acquired from the two clusters, as well as the number of shots Mhigh, having an index in the range [ns, ..., Ns−1], which are not yet acquired from the two clusters, are counted (block 709). If the cluster cn, which is assigned to the last measured respiratory position, is a central, as is assumed in the present case, ("n" in query 711), then the central cluster cn, if Mlow is greater than Mhigh, grows from its smallest already acquired shot index toward ns=0, or kmin, respectively ("n" in query 719), in which the largest of the not yet acquired shot indices is acquired, which is smaller than the smallest already acquired shot index (block 723). Otherwise (Mhigh is greater than Mlow) ("y" in query 719) the cluster cn grows from its largest already acquired shot index toward Ns−1, or kmax, respectively, in which the smallest of the shot indices that is larger than the largest already acquired shot index is acquired (block 721).

In any case, after an acquisition of a shot in one of the blocks 715, 717, 721 and 723, it is checked in query 725 whether all Ns desired shot indices are already acquired in the selected cluster combination. If this is the case ("y" in query 725), the measurement is complete (block 727), and can be stopped; if not ("n" in query 725), then the process is continued with a new navigator measurement. In this manner, the termination criteria remains unchanged with respect to the original version of PAWS; as soon as an arbitrary group of two adjacent clusters (2-bin) has acquired all of the shot indices that are to be measured, the measurement is terminated, because the overall variation of the respiratory position is limited thereby to the acceptance window.

Figure 7:
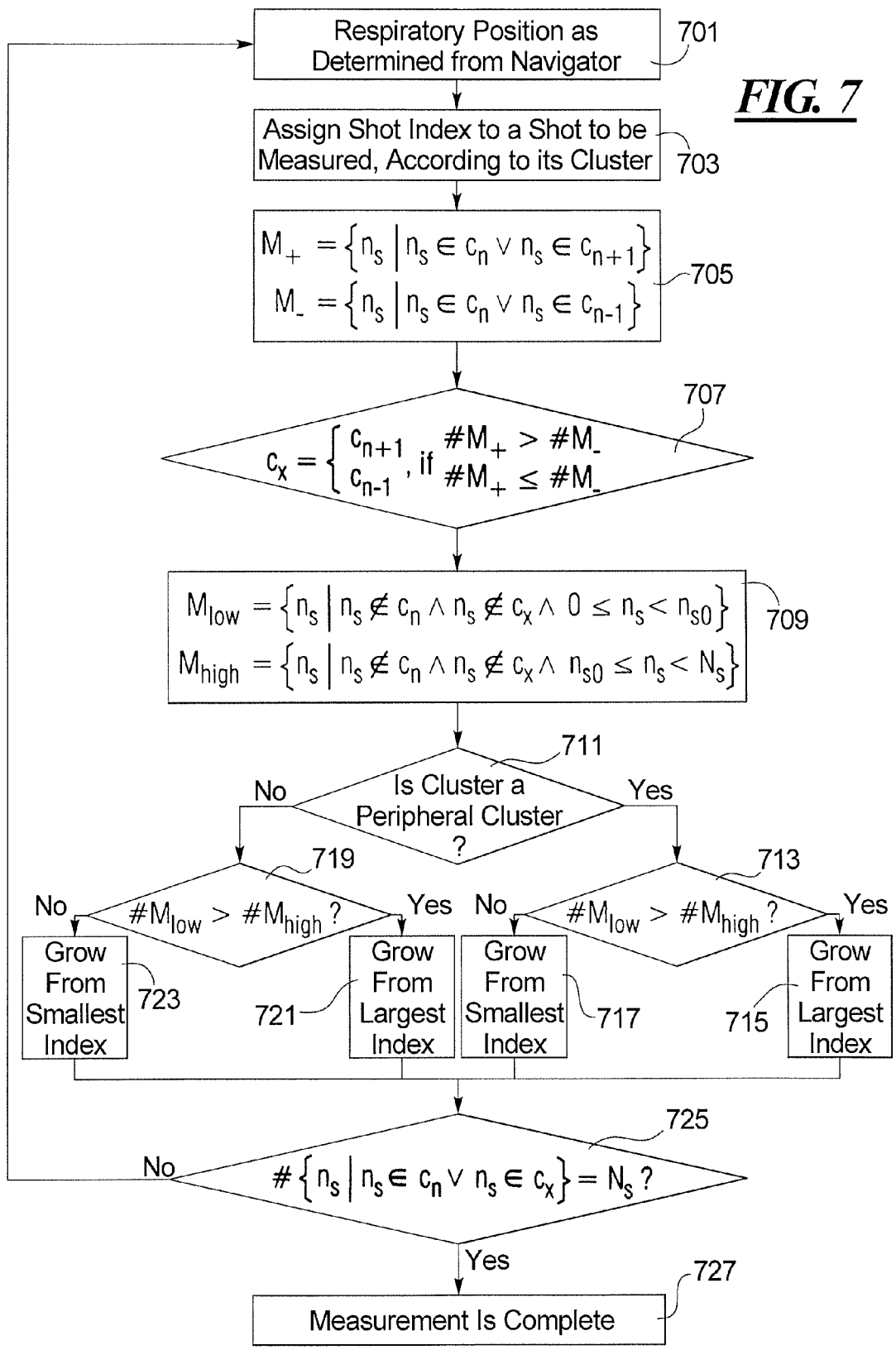
FIG. 7 is a flow chart for the optimized 2-bin PAWS.

In the flowchart in FIG. 7, which summarizes the algorithm described above, the usual symbols of set theory are used:

{.} means a quantity.

{xs|...} ... means the set of all indices shot xs "... applies to ..."

∈ means "is an element of".

{.} ... denotes the number of elements of the set.

^ ... logical symbol for "and".

logical symbol for "or".

This optimal 2-bin version of PAWS unites the high degree of efficiency of the original 2-bin PAWS version with the reduced artifact susceptibility of the original 3-bin variation. The new algorithm actively pushes the segment borders away from particularly movement sensitive k-space centers toward k-space peripheries.

In the following comparison of the various PAWS varieties, it is assumed that the overall width of the acceptance window is given. With an n-bin variation, this acceptance window is spanned by n successive clusters of the respiratory position range. As an example, each cluster is assigned a respiratory position range, the width of which corresponds to $1/n^{th}$ of the acceptance window. This differs in comparison, for example, with the Appendix A in the MRM article by Jhooti et al., already cited above, in which the width of the respiratory position range of a cluster is set to be equal to the navigator resolution. With the latter approach, the overall width of the acceptance window is n×the navigator resolution, and increases with the number of bins. This makes it difficult to carry out a fair comparison of different bin-variations.

The efficiency of the new 2-bin variation, described above, is optimal in the sense that as soon as a respiratory position, in a range covered by two adjacent clusters, is measured Ns times, all Ns shots are recorded, and thus the measurement can be stopped. This property is shared by both the new 2-bin variation and the original 2-bin variation, and is distinguished from the original 3-bin variation and the 3-bin variation from the writings by Nuval et al., cited above.

In contrast to the original 2-bin variation, the probability of cluster borders existing in the vicinity of the movement sensitive k-space center is significantly reduced.

This is visible in FIG. 6, in which, as is normal, each line corresponds to a cluster cn. These are disposed in the vertical plane corresponding to their respiratory position range. In the horizontal plane the phase encoding index is ky, or, respectively, in the general depiction, applied as the shot index ns. The grey shaded bars indicate the ky lines or shots, respectively, acquired from a cluster. The upper portion of FIG. 11b refers to the MRM articles by Jhooti et al. cited above, which represent the selection of the phase encoding lines of the original 2-bin variation at the end of the measurement. In the lower portion, the corresponding presentation of the new 2-bin variation is depicted. It can be seen that the number of times a specific respiratory position is measured is the same in both plots. In the original PAWS method depicted in the upper portion, the cluster border is in the vicinity of the k-space center. In the new variation, depicted in the lower portion, it is displaced to a significant degree toward the periphery of the k-space. In FIG. 6, the cluster borders are highlighted in each case with an oval drawn with a broken line.

This problem is largest when the respiratory positions, which are assigned to the two last clusters, are measured with approximately the same frequency, and the central, particularly movement sensitive, shot, having the shot index ns0, or ky=0, respectively, lies precisely in the center of the index range. In this case, the cluster border lies precisely in the k-space center (ky=0). The new version deals with this particularly important case in an optimal manner: the new cluster borders lie at ca. +25% and +75% of the value range, and are thus maximally distanced from the movement sensitive k-space center.

With an asymmetric scanning of the k-space as well, the new 2-bin variation presented herein functions in an optimal manner in the sense that, with the given number of scans occurring for the central cluster, the segment borders are distanced from the central, particularly movement sensitive shot, having a shot index ns0, or ky=0, respectively, to the maximum extent. Thus, the new version, for all practical purposes, always functions better than the original 2-bin version. The reason for this is that the symmetrical distribution of the shots about the central shot ns0 is actively incorporated in the decision process of the algorithm.

Then, and only then, if the number of scans which occur in the final central cluster is less than the number of scans occurring in the final peripheral cluster, a cluster border may exist in the vicinity of the k-space center. In this case, this border may lie closer to the k-space center than with the original version. This case, however, is extremely unlikely with a reasonable distribution of the acceptance window and a static distribution of the respiratory position in the vicinity of the most probable respiratory position, and has not been observed in our numerous measurements made using the new 2-bin variation. By means of an expansion, similar to the modification b), from one of the two documents cited above by Nuval et al., this case can even be entirely prevented: one restricts the termination criteria in such a manner that the central final cluster must have either acquired a minimum percentage of all shots Ns, or the peripheral final cluster must have acquired all shots Ns. It can be seen that the symmetrical distribution about the k-space center in the new 2-bin algorithm is inherent thereto, and need not be stipulated (in contrast to the 3-bin variations in the prior art).

It should also be mentioned that the borderline case of "no respiration" is managed in an optimal manner with the new 2-bin algorithm (as well as with the original version): all shots are acquired from a single cluster, and thus there are no cluster borders, regardless of whether this cluster is a central or a peripheral cluster.

Figure 8:
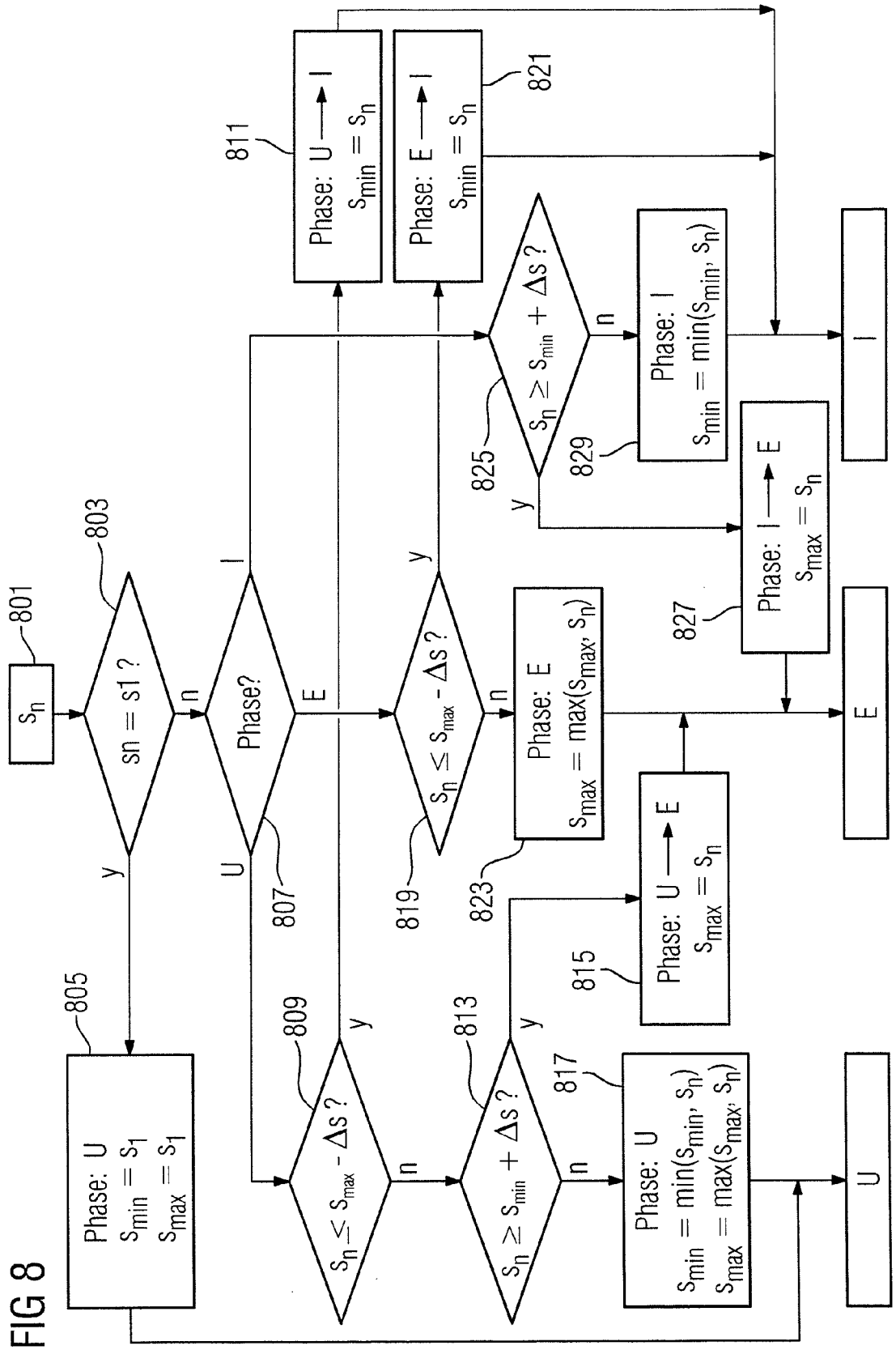
FIG. 8 is a flow chart for a method according to the invention for determining the respiratory phase.

FIG. 8 shows, in a schematic manner, a flow chart for a method for determining the respiratory phase.

For this purpose, a series of measured physiological signal points $(s_1, s_2, \ldots, s_n)$ is given, which correspond to the respiratory positions. In the case of $s_n$, this can be, for example, the last respiratory position measured with the navigator sequence at the point in time $t_n$. $s_{n-1}$ is the respiratory position measured directly prior to this at the point in time $t_{n-1}$, etc. The measurements are afflicted with noise. Each measurement point $s_n$ can therefore be described as:

$$s_n = q_n + n_n,$$

wherein $q_n$ is the unknown, actual physiological state (thus, in the example, the diaphragm position at the point in time $t_n$) and $n_n$ is likewise, the unknown noise.

Without limitation to the general condition, it is further assumed that a local maximum of the series $(q_n)$ corresponds to a state at the end of the exhalation (end-expiration state), and a local minimum of the series $(q_n)$ corresponds to a state at the end of the inhalation (end-inspiration state). This stipulation is made in order to keep the description simple. If the signal course is reversed, such as with the measurement of the chest size using a respiratory belt, then all signal points $s_n$ can simply be multiplied by $-1$, and one proceeds analogously.

The aim of the algorithm is to determine the respiratory phase at an arbitrary point in time $t_n$ from the previous measurements, without knowing the physiological signal points $(s_{n+1}, s_{n+2}, \ldots)$ at the later points in time $n+1, n+2, \ldots$. The respiratory phase is a triplet in this case, which can assume the states {"unknown" (U), "exhalation" (E), and "inhalation" (I)}. For this, the state "unknown" is only assumed at the beginning. As soon as it is abandoned, it is never again obtained.

If the series $(q_n)$ were already known, this problem would be trivial. From $q_n > q_{n-1}$ exhalation (expiration) could be assumed, and $q_n < q_{n-1}$ would imply inhalation (inspiration). In the case of $q_n = q_{n-1}$, the previous state would be retained.

Another input in the algorithm is a threshold parameter $\Delta s$, which—roughly speaking—distinguishes noise from a change in the signal course resulting from the respiratory phase. $\Delta s$ can, for example, be determined by a one-time calibration measurement of the standard deviation of the series $(s_n)$. In our implementation, the empirical value $\Delta s = 4$ mm is used, if it is the case that the navigator measures a diaphragm position.

The algorithm can be interpreted as a status machine (in German, also referred to as a "finite automat," and in English as a "finite state machine" (FSM)).

FIG. 8 illustrates the algorithm using a flow chart.

For this purpose, a physiological signal point $s_n$ (the respiratory signal) is measured (block 801). If the measured signal point $s_n$ is the first measured signal point ($s_n = s_1$), then first, the state "unknown" is assigned ("y" in query 803). Thus, the initial state of the respiratory phase is "unknown."

If the final state machine is in this state, then both a prior maximum measured signal value $s_{max}$, as well as a prior minimum measured signal value $s_{min}$ as of the last change to the respiratory phase, is recorded.

With the measurement of the first signal point $s_1$, the following initialization occurs (block 805):

Phase="unknown" (U); $s_{min} = s_1$; $s_{max} = s_1$. Each new measurement $s_k$ where k>1 ("n" in query 803) can be a transition in the respiratory phase, or trigger the state "exhalation" (E) or "inhalation" (I). For this, first the momentary respiratory phase, i.e. the respiratory phase to which the last signal point was assigned, is queried (query 807).

According to the first measurement $s_1$, as stated, the respiratory phase "unknown" (U) is the momentary respiratory phase. From here, a transition to the inhalation state (I) occurs, if $s_k \leq s_{max} - \Delta s$ ("y" in query 809). Thus, the current respiratory phase is "inhalation" (I), and the minimum measured signal value in this respiratory phase is updated to $s_{min} = s_k$ (block 811). $s_{min}$ is a variable in this case, which indicates the minimal signal value as of the current transition to the state "inhalation" (I).

If $s_k > s_{max} - \Delta s$ ("n" in query 809), then a transition to the state "exhalation" (E) occurs, if $s_k \geq s_{min} + \Delta s$ ("y" in query 813). Thus, the current respiratory phase is "exhalation" (E) and the maximum measured signal value is this respiratory phase is updated to $s_{max}=s_k$ (block 815). $s_{max}$ is a variable which indicates the maximum signal value as of the current transition to the state "exhalation" (E).

If neither the query 809, nor the query 813 is correct ("n" in query 813), then $s_k$ does not trigger a state transition, but instead the respiratory phase "unknown" is also the current respiratory phase and the variables $s_{min}$ and $s_{max}$ are updated:

$$s_{min}=\min(s_{min},s_k); s_{max}=\max(s_{max},s_k).$$

If the finite state machine is in the state "exhalation" (E) ("E" in query 807), then with the measurement of the next signal point $s_1$, either the state "exhalation" (E) can be retained, a transition to the state "inhalation" (I) occurs. For this, query 819 is carried out, which checks whether $s_1 \leq s_{max} - \Delta s$. If yes ("y" in query 819), then the respiratory phase currently changes to "inhalation" (I), and the variable $s_{min}$ is updated to $s_{min}=s_1$ (block 821). If not ("n" in query 819), then the state "exhalation" (E) is retained for the current respiratory phase, and the variable $s_{max}$ is updated to $s_{max}=\max(s_{max}, s_1)$ (block 823).

$s_{min}$ is a variable indicating the minimum signal value as of the current transition to the state "inhalation" (I). The initialization with the current measured signal point is independent of whether the transition occurs from the state "unknown" (U) or "exhalation" (E).

If the finite state machine is in the state "inhalation" (I) ("I" in query 807), then with the measurement of the next signal point $s_m$, either a transition to the state "exhalation" (E) can occur, or the state "inhalation" (I) is retained. For this, the query 825 is carried out, which checks whether $s_m \geq s_{min} + \Delta s$. If yes ("y" in query 825), then the respiratory phase currently changes to the state "exhalation" (E), and the variable $s_{max}$ is updated to $s_{max}=s_m$ (block 827). If not ("n" in query 825), then the state "inhalation" (I) is retained for the current respiratory phase, and the variable $s_{min}$ is updated to $s_{min}=\min(s_{min}, s_m)$ (block 829).

In this manner, each new signal point $s_n$ is assigned to an unambiguous respiratory phase. This allocation is implicitly dependent on the momentary state of the finite state machine and the variables $s_{min}$ and/or $s_{max}$ from the previously measured signal points, but not on the future $s_{n+1}, \ldots,$ which are unknown in a prospective decision. As soon as the initial state "unknown" has been abandoned once, then the prospective gating can be initiated, taking into account the binary respiratory phase.

It should be noted here, that a digital filtering or an evening out of the series (sn) can be entirely eliminated here.

By means of this method, the respiratory phase in a prospective gating method can be determined, also by means of respiratory positions measured by means of navigator measurements, and used in order to keep the actual variations to the respiratory positions in the final measurement data that are used for the image reconstruction to a minimum.

Figure 9:
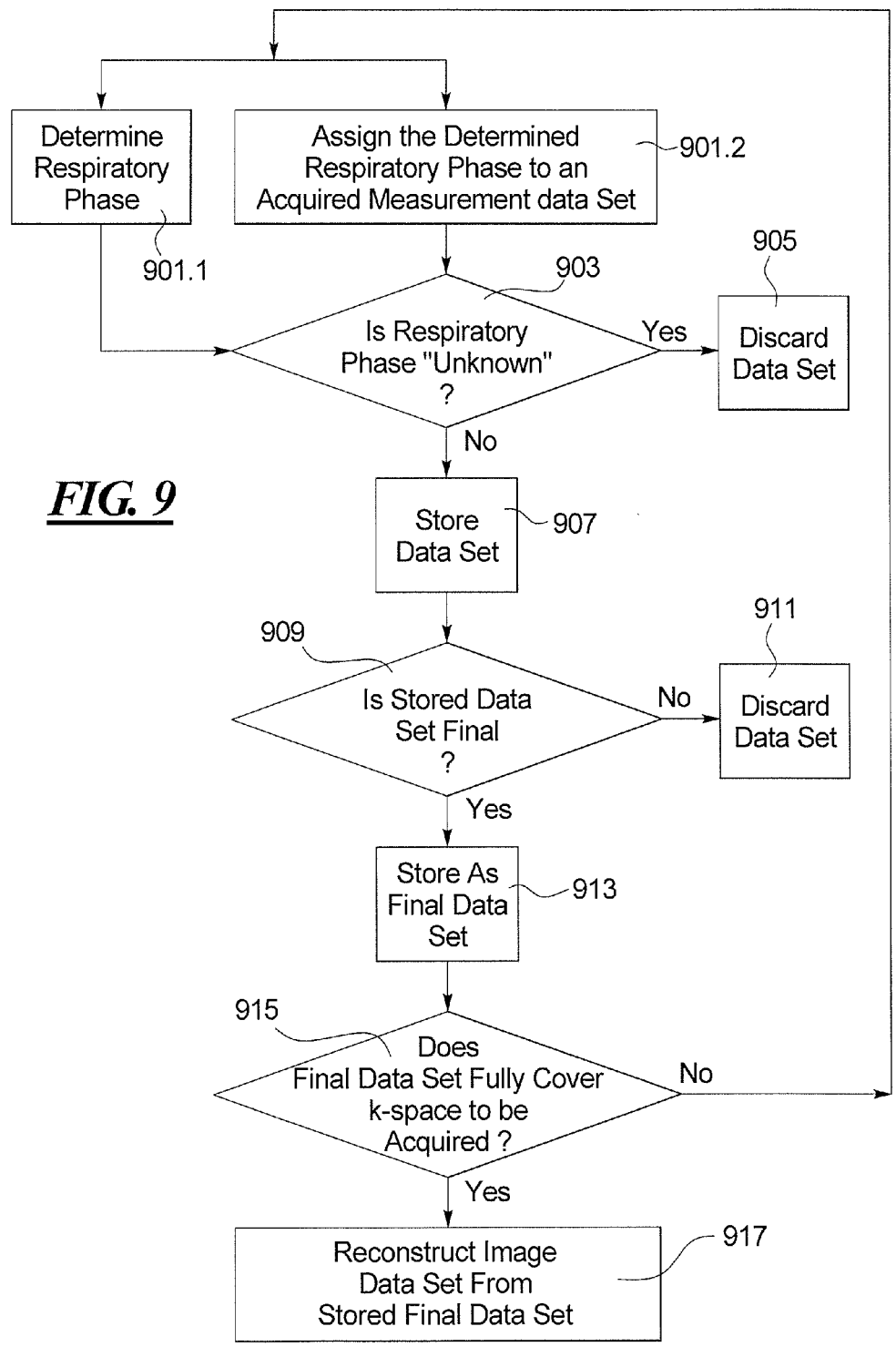
FIG. 9 is a flow chart of a method according to the invention.

A flow chart of a method for the acquisition of a measurement data set in individual measurements is depicted schematically in FIG. 9, wherein, for each individual measurement, a respiratory position and a respiratory phase are determined, based on which it is decided whether the individual measurement is to be recorded in a final measurement data set from which an image data set is reconstructed.

For this, a physiological signal, the respiratory position, is measured, and, for example, as was described above in reference to FIG. 8, an associated respiratory phase is determined (block 901.1). Subsequently, an individual measurement for the measurement data set that is to measured is acquired, which is assigned to the previously determined respiratory phase and the measured respiratory position (block 901.2).

If the assigned respiratory phase is "unknown" (U) ("y" in query 903), the data of the individual measurement are discarded, or not recorded in a final measurement data set, respectively, from which an image data set for the examination subject that is to be measured is reconstructed (block 905).

If the assigned respiratory phase is not "unknown" (U) ("n" in query 903), then the measurement data are stored together with their respiratory phase and respiratory position (block 907).

By means of the query 909, it is decided, based on the respective assigned respiratory position and respiratory phase, and by means of a selected algorithm, whether the acquired measurement data are to be recorded in the final measurement data set ("y" in query 909) and accordingly, stored in a possible final measurement data set (block 913), or whether the acquired measurement data can be discarded in block 911 ("n" in query 909). Depending on the algorithm used, it is possible to store numerous possible final measurement data sets, wherein the measurement is stopped when one of these possible measurement data sets fully scans the desired k-space.

If the measurement data stored up until this point in the final measurement data set fully cover the entire k-space that is to be acquired (query 915), then the process stops, and an image data set is reconstructed from the final measurement data set (block 917), and if not ("n" in query 915), then a respiratory position and a respiratory phase are determined, and an associated individual measurement is acquired. In this manner, respiratory positions and respiratory phases are determined, and associated individual measurements are acquired, until the k-space corresponding to the examination subject that is to be examined has been fully recorded.

Which criteria are to be used in query 909 depends on the selected algorithm. By way of example, an acceptance/rejection algorithm can be selected in which the k-space that is to be recorded for the image reconstruction is measured by segments in individual measurements (block 901.2). Each measurement of a segment is assigned a physiological data point (block 901.1). A physiological data point is characterized thereby by means of a respiratory position and a respiratory phase. A specific data segment is then accepted in query 909, i.e. it is used later in block 917 for image reconstruction, only if the respiratory position of the physiological data point assigned thereto lies within an acceptance window, and the respiratory phase of the physiological data point assigned thereto assumes a given state, e.g. "inhalation." If this is the case, then two final data sets can be stored thereby, which each accept a different respiratory phase. In this case, the measurement is stopped (block 917), if one of the two final measurement data sets fully comprises the k-space that is to be acquired.

The requirement of a concrete respiratory phase distinguishes the presented method from the prior art. If one of the two conditions is not met, the measurement of the segment is repeated ("n" in query 915). The respiratory position of the physiological data point is, for example, recorded, as is the case in the prior art, with a navigator sequence, which is executed either directly before or directly after the measurement of the segment. In certain k-space trajectories (such as radial or spiral) the respiratory position can also be extracted directly from the measurement data. Such a method can be called a self navigated or "self gated" method. The respiratory phase assigned to physiological data point is determined, in contrast to this, from the series of the previously occurring navigator measurements.

The type of k-space segmentation does not play a role in the method. Because the navigator sequence frequently interrupts the stationary steady state of the imaging sequence, one preferably inserts the navigator at such positions in the sequencing in which the stationary steady state is necessarily interrupted for other reasons, e.g. due to a fat saturation pulse, or when waiting for another physiological signal, such as an ECG trigger.

In another embodiment, a PAWS algorithm can be selected, wherein the prerequisites for the imaging sequence, with which the individual measurements are acquired, (as described above, summarized once again) are:

a) An individual measurement is a shot, wherein a "shot" is understood to mean all of the measurement data of the imaging sequence, which are acquired following a specific navigator sequence (and prior to the following navigator sequence). These data are assigned to the respiratory position measured with the navigator sequence, and the determined respiratory phase. In general, one selects a constant time period for the length of the shots, but this is not absolutely necessary.

b) The number of shots required for a complete recording of the k-space that is to be scanned is Ns.

The prerequisites a and b are sufficient for automatically establishing the final acceptance window. Should additional "phase ordering" be carried out, the following two prerequisites c and d are needed in addition:

c) Each shot can be assigned a scalar, which describes the neighborhood in the k-space. The shot index ns in [0, . . . , Ns−1] is classified in accordance with this scalar.

d) There is a distinctive shot having the shot index ns0 in [0, . . . , Ns−1] having a maximum movement sensitivity. Accordingly, the movement sensitivity increases in the range [0, . . . , ns0], and decreases in the range [ns0, . . . , Ns−1].

For this, each navigator measurement is assigned a (scalar) respiratory position and a binary respiratory phase ("inhalation," "exhalation"), or, respectively, a respiratory phase from the triplet ("inhalation," "exhalation," "unknown"), as described above. The prerequisite for this is that a navigator measurement, which occurs temporally after the individual measurement, to which the respiratory phase is to be assigned, is not necessary for determining the respiratory phase. This can be obtained, for example, with the method described in reference to FIG. 8.

One embodiment of the method, which uses a generalized PAWS algorithm, presented above, is characterized by the following properties:

a) A cluster is characterized by a respiratory position range (or acceptance range) and a respiratory phase. It comprises all shot indices (block 913), which have already been measured after a respiratory position in the respiratory position range assigned to the cluster, and the respiratory phase assigned to the cluster have been measured.

b) There are two cluster sets. The first cluster set consists of so-called inspiratory clusters (i.e. clusters assigned the cluster phase "inhalation"). The second set consists of so-called expiratory clusters (i.e. clusters having the respiratory phase "exhalation" assigned thereto). Data with undetermined respiratory phases are discarded.

c) The clusters are classified according to their respiratory position range. The respiratory position ranges of different clusters are disjunctive, and "gap-less." For each measured respiratory position, there exists, therefore, exactly one cluster in which this respiratory position falls within its acceptance range. Furthermore, the respiratory position ranges of n successive clusters each cover a respiratory position range, which is coordinated to the desired final width of the acceptance window.

d) As soon as an arbitrary group of n adjacent clusters comprises a set of all of the shot indices [0, . . . , Ns−1] that are to be measured (query 915), the measurement can be stopped (block 917), because the overall variation to the respiratory position is thus limited to the acceptance window, and all of the measurement data belonging to the group of n adjacent clusters during a respiratory phase have been measured.

The characteristics a)-d) are sufficient for an automatic location of the final acceptance window. With the characteristic e a phase ordering can additionally be obtained.

e) Each cluster is assigned a starting position in the form of a shot index (also referred to as starting index ns_seed) in the interval [ns0, . . . , Ns−1]. The cluster grows, starting from the starting position, in such a manner that the index range covered by the cluster is without gaps. Optimally, for this the index range is continued at the range borders in a periodic or cyclical manner, as described above in reference to the optimized 2-bin PAWS. The decision of whether a cluster grows toward smaller or larger shot indices takes into consideration, in general, the shot indices already acquired from adjacent clusters. The aim is to select an index in such a manner that an arbitrary group of n adjacent clusters, which contains the cluster to which the currently measured respiratory position is assigned, is complete to the greatest extent possible, i.e. comprises the larges possible number of different shot indices. The optimal distribution of the starting positions between adjacent clusters depends on the number of bins.

The embodiment described above requires that the final accepted data be completely measured during the respiratory phase "inhalation," be completely measured during the respiratory phase "exhalation."

In another embodiment, which likewise uses a generalized PAWS algorithm, presented above, an exception is allowed: In the particularly quiet phase at the end of the exhalation, and with the initiation of the inhalation, the image reconstruction with data acquired during exhalation and inhalation is enabled. This means that with the one cluster having the maximum measured respiratory position of a first respiratory phase, a second respiratory phase is regarded as adjacent to the cluster having the maximum measured respiratory position, although the two clusters are assigned to different respiratory phases. The characteristics of this alternative are:

a) As before, a cluster is characterized by a respiratory position range (or acceptance range, respectively) and a respiratory phase. It comprises all shot indices (block 913) that have already been measured after a respiratory position in the respiratory position range assigned to the cluster, and the respiratory phase assigned to the cluster, have been measured.

b) Directly adjacent clusters are assigned the same respiratory phase, with one exception: The expiratory cluster having the maximum respiratory position and the inspiratory cluster having the maximum respiratory position can be regarded as adjacent as long as c) is complied with.

c) Clusters having the same respiratory phase are arrayed in accordance with their respiratory position range. The respiratory position ranges of different clusters having the same respiratory phase are disjunctive and "gap-less." The two adjacent clusters having different respiratory phases have either the same respiratory position range, or the respiratory position range of the inspiratory cluster is connected, without gaps, to the respiratory position range of the expiratory cluster, until it reaches smaller respiratory positions. Both rules require, in general, the insertion of empty clusters (i.e. of clusters having an acceptance range/respiratory phase during which no data have yet been acquired).

It should be noted here, that the neighborhood at the transition between expiratory and inspiratory clusters is normally temporary. If a more extreme respiratory position is measured, the existing neighborhood relation between expiratory and inspiratory clusters, each having a maximum respiratory position, is interrupted, and further clusters are inserted.

d) As soon as an arbitrary group of n adjacent clusters comprises a set of all of the shot indices [0, . . . , Ns−1] that are to be measured, the measurement can be stopped (block 917), because the overall variation to the respiratory position is thus limited to the acceptance window.

The characteristics a)-d) are sufficient for an automatic location of the final acceptance window. With the characteristic e, a phase ordering can also be obtained.

e) Each cluster is assigned a starting position as the shot index (also referred to as "start index ns_seed") in the interval [ns0, . . . , Ns−1]. The cluster grows starting from the starting position, in such a manner that the index range covered by the cluster is without gaps. Optimally, thereby, the index range is continued at the range borders in a periodic or cyclical manner (as described above in reference to the optimized 2-bin PAWS). The decision, whether a cluster grows toward smaller or larger shot indices, also includes, in general, the shot indices already acquired from adjacent clusters. The aim is to select an index in such a manner that an arbitrary group of n adjacent clusters, which contain the cluster assigned to the current measured respiratory position, is as complete as possible, i.e. comprises as many different shot indices as possible. The optimal distribution of the starting positions between adjacent clusters depends on the number of bins.

If a specific pattern of starting positions is obtained, than this should also be maintained in the transitions between expiratory and inspiratory clusters. This may require the insertion of empty clusters.

In another embodiment example, a diminishing variance algorithm (DVA) is selected as the determining algorithm for query 909. In his case, a possible expansion of the DVA can be implemented, taking into consideration the respiratory phase, in the following manner:

Respiratory positions that have been measured during the respiratory phase "exhalation" and the respiratory phase "inhalation" are recorded in separate histograms. At the end of the initial phase (i.e. after all desired k-space data are recorded completely, without gating, together with the respective measured respiratory position and respiratory phase), the most frequent respiratory phase is first determined, and the mode for each of the two histograms is determined. In the subsequent re-acquisition phase, first such k-space data that have been acquired during the "unknown" phase are re-acquired. With each new measurement, the histograms are updated (and thereby, the modes, respectively), and the current most frequent respiratory phase is determined. As soon as there are no more k-space data having the respiratory phase "unknown," the mode of the histogram having the most entries overall is selected as the basis for the re-acquisition (block 913). As is the case in the prior art, the k-space data having respiratory positions deviating to the greatest extent from this mode are taken into consideration for the re-acquisition. Due to the digitalization of the respiratory signal, there are normally numerous k-space data packets ("shots" in the notation used above), having the same respiratory position. Among the shots that deviate to the greatest degree from the selected mode, there may be some that have been measured in different respiratory phases. If this is the case, then (in deviating from the prior art) the repetition of the shots is initiated, of those that were measured during the less frequent respiratory phase. The termination criterion is either a time limit and/or that all of the measurement data have been measured during one respiratory phase, and the respiratory positions lie within an acceptance window of a given width (block 917). It can be seen that, due to the continuous updating of the histogram, the most frequent respiratory phase can, at least in theory, change during the runtime.

FIG. 10 shows, in an exemplary fashion, an embodiment example of a method described in reference to FIG. 9, in conjunction with the new optimized 2-bin PAWS. For this, the cluster diagram of a new 2-bin PAWS measurement is shown, with the given differentiation of the respiratory phases. Each horizontal bar corresponds to a cluster. These are arranged vertically with respect to their respiratory position range. The shot index ns is recorded in the horizontal axis. The respiratory position AP is recorded along the vertical axis. A cluster contains, respectively, the shots acquired from said cluster, along the horizontal axis. The left-hand diagram shows the cluster having the respiratory phase "exhalation" (E), and the right-hand diagram shows the cluster having the respiratory phase "inhalation" (I).

In this case, the diaphragm position measured with a navigator serves as the respiratory signal. The resolution was 0.5 mm. Accordingly, the respiratory signal is digitalized into 0.5 mm units. Because only relative positions are measured with the navigator, in relation to a reference state, the zero point of the vertical axis is selected such that "0" corresponds to the maximum measured end-expiration signal.

The width of the final acceptance window is set by the user at ±1 mm. Due to the digitalization to a 0.5 mm grid pattern, it therefore comprises 5 different respiratory positions. These are distributed to peripheral and central clusters such that the acceptance range of a peripheral cluster comprises three different respiratory positions, and the one central cluster comprises two.

The two final clusters are indicated with thinner lines. The respiratory phase of these two clusters is "exhalation" (E). The acceptance range of the central final cluster contains the respiratory positions at −4.5 mm and −4.0 mm. The acceptance range of the peripheral final clusters contains the respiratory positions at −3.5 mm, −3.0 mm, and −2.5 mm.

One sees in FIG. 10 that only relatively few signal points are excluded by the differentiation of the respiratory phases. The total number of excluded shots is equal to the number of shots assigned to the two encircled clusters having the respiratory phase "inhalation" (I), the acceptance range of which corresponds in each case to that of a final cluster.

A measured respiratory signal is depicted in an exemplary manner in FIG. 11, as occurred in the measurement from FIG. 10. For this purpose, the time t is recorded at the left, and the respiratory position is recorded at the top. The measured respiratory positions are recorded as circles or triangles, depending on whether the respective respiratory position is assigned to the phase "inhalation" (circles) or "exhalation" (triangles). The acceptance window AF is indicated at the left edge of the diagram, and by continuous lines. Furthermore, the overall variation V1 and the overall variation V2 to the respiratory position during the acquisition of the final measurement data sets, which result when one undertakes a differentiation of the respiratory phase (V1) or does not undertake such differentiation of the respiratory phase (V2), is indicated with punctiform lines. As one sees, the overall variation V2, in which adjacent respiratory positions can lie in adjacent clusters, independently of their respiratory phase, is much larger than when, as is the case here, only respiratory positions having the same respiratory phase can lie in adjacent clusters.

The imaging sequence here concerns a 3D double echo-played gradient echo sequence. This acquires, directly after a navigator sequence, in each case, 35 k-space lines having different values for the two phase encoding gradients. Directly after 35 k-space lines, another navigator sequence is carried out. An inherent property of the prospective gating is that the decision process can only be based on previous navigator measurements. However, use the discrepancy between previous and subsequent navigator measurements can be retrospectively used as the measure for the actual variation to the respiratory position during the imaging measurement.

If the prospective decision is based exclusively on the respiratory position, as is the case with the prior art, then the actual variation to the respiratory position is V2 while the image data used for the reconstruction are significantly larger than the acceptance window AF. For the three respiratory cycles shown, this lies between the punctiform lines with a spacing of V2. For the overall measurement, it is even larger.

The four circled signal points in FIG. 11 have a respiratory position, which lies within the acceptance window, but are not used in the presented method for the final image reconstruction, because at this point, the data measured directly after these signal points are assigned to other clusters. The exclusion of these signal points leads to a significant reduction to the actual total variation to the respiratory position. For the three illustrated respiratory cycles, it lies between the broken lines (spacing V1) and is only slightly larger than the acceptance window.

By means of the detection and differentiation of the respiratory phase used here, a significant reduction of the actual respiratory movement during the imaging measurement and the thereby associated respiratory artifacts is thus obtained through a relatively small reduction in efficiency.

In the prior art, one possibility for reducing the respiratory movement during the imaging measurement is to reduce the size of the acceptance window. In order to obtain a corresponding reduction to the actual respiratory movement of ca. 50%, as is the case in FIG. 11, a reduction to the size of the acceptance window of likewise ca. 50% would also be necessary, which would result in a significant reduction to the efficiency.

One further possibility in the prior art would be to use double gating methods, known from the article cited above, by Sachs et al. "Real-Time Motion Detection in spiral MRI Using Navigators," MRM 32: Pages 639-645 (1994). This, however, is only compatible with the simple acceptance-rejection algorithm. With the use of this method, the disadvantages specified above associated with the acceptance-rejection algorithm (efficiency loss with varying/drifting respiration) must be accepted.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for acquiring a magnetic resonance measurement data set of a breathing subject, comprising:
    operating a magnetic resonance apparatus, in which a breathing subject is located, to acquire a plurality of magnetic resonance data subsets;
    entering the plurality of magnetic resonance data subsets into an electronic memory representing k-space, wherein k-space is comprised of a plurality of segments, and entering the respective magnetic resonance data subsets individually into respective k-space segments;
    also operating said magnetic resonance apparatus to make at least two navigator data acquisitions, before each respective acquisition of said magnetic resonance data acquisitions subset acquisitions, and using said navigator data to determine a respiratory position of the subject, and a respiratory phase of the subject and assigning said respiratory position and phase to the magnetic resonance data subset acquired in the respective acquisition; and
    providing the respiratory position and the respiratory phase to a processor and, in said processor, using the respiratory position and the respiratory phase, assigned to each of the magnetic resonance data subsets, to decide automatically whether a respective magnetic resonance data subset is included or not included in a final magnetic resonance data set from which a magnetic resonance image is to be reconstructed, and making said final magnetic resonance data set available in electronic form at an output of said processor.

2. A method as claimed in claim 1 comprising determining said respiratory phase using navigator data acquired with at least two of said navigator data acquisitions being acquired with a temporal spacing that is substantially smaller than a duration of a respiratory cycle of the breathing subject.

3. A method as claimed in claim 1 comprising, in said processor, using said respiratory phase for each magnetic resonance data subset to assign a designation of "inhaling" or "exhaling" to the respective magnetic resonance data subset.

4. A method as claimed in claim 3 comprising assigning the respective magnetic resonance data subset a designation of "unknown" if neither of said designations "inhaling" or "exhaling" can be assigned to the respective magnetic resonance data subset.

5. A method as claimed in claim 4 comprising, in said processor, not including any magnetic resonance data subsets, in said final magnetic resonance data set that have an "unknown" designation.

6. A method as claimed in claim 1 comprising, in said processor, including a respective magnetic resonance data subset in said final magnetic resonance data set only if a respiratory position thereof is within a predetermined acceptance window and the respiratory phase thereof has a predetermined value.

7. A method as claimed in claim 1 comprising:
    in said processor, subdividing the respiratory position and the respiratory phase of the subject into a plurality of predetermined clusters, each cluster encompassing a predetermined respiratory range of said respiratory positions and said respiratory phases of the subject;
    operating said magnetic resonance apparatus to acquire said magnetic resonance data subsets as a plurality of shots, with the magnetic resonance data of each shot filling a predetermined number of lines in k-space that is less than an entirety of all lines in k-space, and each shot exhibiting a three-dimensional k-space trajectory in k-space, with respectively different shots filling respectively different lines in k-space such that each shot fills a predetermined k-space region;
    in said processor, assigning a respective shot index to each of said shots that designates a sensitivity of the respective shot to movement by the subject, and assigning said shot indices to the respective shots with adjacent shot indices being assigned to respective shots, among said plurality of shots, that exhibit an incrementally different sensitivity to said movement, with a shot having a highest sensitivity to motion receiving a shot index in the middle of the total index range;

in said processor, assigning a range of adjacent shot indices to each of said clusters, that causes shots to be assigned to specific clusters where said range of shot indices is initially empty;

in said processor assigning a start index to each of said clusters;

operating said magnetic resonance apparatus to acquire the respective shots by (A) acquiring said navigator data, (B) in said processor, selecting a specific cluster in the respective respiratory range in which said navigator data indicate the respiratory position and the respiratory phase occur, (C) from said processor, selecting a shot to be acquired that has a shot index that borders the shot index range of said specific cluster, or if the shot index range is empty, selecting the shot that has the start index of said specific cluster and (D) acquiring said shot to be acquired and assigning said shot to the specific cluster;

repeating (A), (B), (C) and (D) until at least two bordering clusters, that encompass adjacent respiratory regions of the subject, collectively encompass the shot indices of all said shots in said measurement data set; and reconstructing an MR image from magnetic resonance data of said shots assigned to said two bordering clusters.

8. A method as claimed in claim 7 comprising, in said processor, selecting said shot to be acquired that causes the respective k-space region, to be filled with magnetic resonance data of the shot to be acquired, to be filled as uniformly as possible along a filling criterion selected from the group consisting of respective axis of said three-dimensional k-space trajectory, and different sides of the respective k-space region.

9. A method as claimed in claim 7 wherein said lines in k-space are oriented along a readout axis of a readout gradient field generated in said magnetic resonance data acquisition unit, and wherein the respective k-space is filled such that different lines acquired by a particular shot are disposed substantially radially in a plane that is perpendicular to said readout axis.

10. A method as claimed in claim 9 comprising, in said processor, dividing each k-space region into sectors that are defined with respect to a distance thereof from a center of k-space, with a k-space line located in each sector for each of said shots.

11. A method as claimed in claim 10 comprising, in said processor, selecting the respective k-space trajectories so that each k-space trajectory enters data into a k-space line, that is different for each of said shots, in a series corresponding to a neighborhood of the respective sectors in which the respective k-space lines are located, within a respective k-space region.

12. A magnetic resonance apparatus comprising:

a magnetic resonance imaging device;

a control computer configured to operate said magnetic resonance imaging device, in which a breathing subject is located, to acquire a plurality of magnetic resonance data subsets;

an electronic memory representing k-space;

said control computer being configured to enter the plurality of magnetic resonance data subsets into said electronic memory representing k-space, wherein k-space is comprised of a plurality of segments, by entering the respective magnetic resonance data subsets individually into respective k-space segments;

said control computer being configured to operate said magnetic resonance imaging device to make at least two navigator data acquisitions, before each respective acquisition of said magnetic resonance data subset acquisitions, and to use said navigator data acquisitions to determine a respiratory position of the subject and a respiratory phase of the subject and to assign said respiratory position and phase to the magnetic resonance data subset acquired in the respective acquisition; and said control computer being configured to use the respiratory position and the respiratory phase, assigned to each of the magnetic resonance data subsets, to decide automatically whether a respective magnetic resonance data subset is included or not included in a final magnetic resonance data set from which a magnetic resonance image is to be reconstructed, and to make said final magnetic resonance data set available in electronic form at an output of said control computer.

13. A non-transitory, computer-readable data storage medium encoded with programming instructions, said storage medium being loaded into a computerized control and processing system of a magnetic resonance apparatus, and said programming instructions causing said computerized control and processing system to:

operate the magnetic resonance apparatus, in which a breathing subject is located, to acquire a plurality of magnetic resonance data subsets;

enter the plurality of magnetic resonance data subsets into an electronic memory representing k-space, wherein k-space is comprised of a plurality of segments, entering the respective magnetic resonance data subsets individually into respective k-space segments;

also operate the magnetic resonance apparatus to make at least two navigator data acquisitions, before each respective acquisition of said magnetic resonance data subset acquisitions, and use said navigator data acquisitions to determine a respiratory position of the subject and a respiratory phase of the subject and assign said respiratory position and phase to the magnetic resonance data subset acquired in the respective acquisition; and use the respiratory position and the respiratory phase, assigned to each of the magnetic resonance data subsets, to decide whether a respective magnetic resonance data subset is included or not included in a final magnetic resonance data set from which a magnetic resonance image is to be reconstructed, and make said final magnetic resonance data set available in electronic form at an output of said control and processing system.

* * * * *